United States Patent
Sawyer et al.

(10) Patent No.: US 12,054,558 B2
(45) Date of Patent: Aug. 6, 2024

(54) ANTI-NGLY-1 ANTIBODIES AND METHODS OF USE

(71) Applicant: The Jackson Laboratory, Bar Harbor, ME (US)

(72) Inventors: Alan Sawyer, Bar Harbor, ME (US); Aamir Zuberi, Bar Harbor, ME (US); Cathleen Marie Lutz, Bar Harbor, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 890 days.

(21) Appl. No.: 17/057,236

(22) PCT Filed: May 22, 2019

(86) PCT No.: PCT/US2019/033499
§ 371 (c)(1),
(2) Date: Nov. 20, 2020

(87) PCT Pub. No.: WO2019/226758
PCT Pub. Date: Nov. 28, 2019

(65) Prior Publication Data
US 2021/0139607 A1 May 13, 2021

Related U.S. Application Data

(60) Provisional application No. 62/697,058, filed on Jul. 12, 2018, provisional application No. 62/675,715, filed on May 23, 2018.

(51) Int. Cl.
*C07K 16/40* (2006.01)
*G01N 33/573* (2006.01)
*A61K 39/00* (2006.01)

(52) U.S. Cl.
CPC ............ *C07K 16/40* (2013.01); *G01N 33/573* (2013.01); *A61K 2039/505* (2013.01); *C07K 2317/34* (2013.01); *C07K 2317/565* (2013.01); *C07K 2317/567* (2013.01); *C07K 2317/92* (2013.01); *G01N 2800/52* (2013.01)

(58) Field of Classification Search
None
See application file for complete search history.

(56) References Cited

U.S. PATENT DOCUMENTS

| | | |
|---|---|---|
| 2009/0136483 A1 | 5/2009 | Sabbadini et al. |
| 2009/0285830 A1 | 11/2009 | Adams et al. |
| 2010/0150918 A1 | 6/2010 | Kufer et al. |
| 2016/0311927 A1 | 10/2016 | Eriksson |
| 2018/0000914 A1 | 1/2018 | Valton et al. |

FOREIGN PATENT DOCUMENTS

WO  2018/023136 A1  2/2018

OTHER PUBLICATIONS

Enns et al., Mutations in Ngly1 cause an inherited disorder of the endoplasmic reticulum-associated degradation (ERAD) pathway. Genet Med. Oct. 2014;16(10):751-8. doi: 10.1038/gim.2014.22. Epub Mar. 20, 2014. Erratum in: Genet Med. Jul. 2014;16(7):568. Chen, Rui [added].

Fujihira et al., Lethality of mice bearing a knockout of the Ngly1-gene is partially rescued by the additional deletion of the Engase gene. PLoS Genet. Apr. 20, 2017;13(4):e1006696. doi: 10.1371/journal.pgen.1006696.

He et al., A congenital disorder of deglycosylation: Biochemical characterization of N-glycanase 1 deficiency in patient fibroblasts. Glycobiology. Aug. 2015;25(8):836-44. doi: 10.1093/glycob/cwv024. Epub Apr. 21, 2015.

Li et al., Epitope mapping reveals the binding mechanism of a functional antibody cross-reactive to both human and murine programmed death 1. MAbs. May/Jun. 2017;9(4):628-637. doi: 10.1080/19420862.2017.1296612. Epub Feb. 23, 2017.

*Primary Examiner* — G. R. Ewoldt
(74) *Attorney, Agent, or Firm* — Wolf, Greenfield & Sacks, P.C.

(57) ABSTRACT

Provided herein, in some embodiments, are anti-N-glycanase 1 antibodies and methods of use.

12 Claims, 10 Drawing Sheets
Specification includes a Sequence Listing.

SEQUENCE LISTING

```
<160> NUMBER OF SEQ ID NOS: 46

<210> SEQ ID NO 1
<211> LENGTH: 450
<212> TYPE: PRT
<213> ORGANISM: Artificial Sequence
<220> FEATURE:
<223> OTHER INFORMATION: Synthetic polypeptide

<400> SEQUENCE: 1

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Ile Asn Tyr
            20                  25                  30

Leu Ile Glu Trp Val Lys Gln Arg Pro Gly Gln Gly Leu Glu Trp Ile
        35                  40                  45

Gly Ile Ile Ser Pro Gly Ser Gly Ser Thr Asn Tyr Asn Glu Glu Phe
    50                  55                  60

Arg Gly Arg Ala Thr Leu Thr Ala Asp Arg Ser Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Gly Gly Leu Thr His Tyr Ser Gly Ser Thr Tyr Glu Glu Gly
            100                 105                 110

Phe Asp Phe Trp Gly Gln Gly Thr Thr Leu Thr Val Ser Ser Ala Lys
        115                 120                 125

Thr Thr Pro Pro Ser Val Tyr Pro Leu Ala Pro Gly Ser Ala Ala Gln
    130                 135                 140
```

Thr Asn Ser Met Val Thr Leu Gly Cys Leu Val Gly Tyr Phe Pro
145                 150                 155                 160

Glu Pro Val Thr Val Thr Trp Asn Ser Gly Ser Leu Ser Ser Gly Val
                165                 170                 175

His Thr Phe Pro Ala Val Leu Gln Ser Asp Leu Tyr Thr Leu Ser Ser
            180                 185                 190

Ser Val Thr Val Pro Ser Ser Thr Trp Pro Ser Glu Thr Val Thr Cys
        195                 200                 205

Asn Val Ala His Pro Ala Ser Ser Thr Lys Val Asp Lys Lys Ile Val
210                 215                 220

Pro Arg Asp Cys Gly Cys Lys Pro Cys Ile Cys Thr Val Pro Glu Val
225                 230                 235                 240

Ser Ser Val Phe Ile Phe Pro Pro Lys Pro Lys Asp Val Leu Thr Ile
                245                 250                 255

Thr Leu Thr Pro Lys Val Thr Cys Val Val Val Asp Ile Ser Lys Asp
            260                 265                 270

Asp Pro Glu Val Gln Phe Ser Trp Phe Val Asp Asp Val Glu Val His
        275                 280                 285

Thr Ala Gln Thr Gln Pro Arg Glu Glu Gln Phe Asn Ser Thr Phe Arg
290                 295                 300

Ser Val Ser Glu Leu Pro Ile Met His Gln Asp Trp Leu Asn Gly Lys
305                 310                 315                 320

Glu Phe Lys Cys Arg Val Asn Ser Ala Ala Phe Pro Ala Pro Ile Glu
                325                 330                 335

Lys Thr Ile Ser Lys Thr Lys Gly Arg Pro Lys Ala Pro Gln Val Tyr
            340                 345                 350

Thr Ile Pro Pro Pro Lys Glu Gln Met Ala Lys Asp Lys Val Ser Leu
        355                 360                 365

Thr Cys Met Ile Thr Asp Phe Phe Pro Glu Asp Ile Thr Val Glu Trp
370                 375                 380

Gln Trp Asn Gly Gln Pro Ala Glu Asn Tyr Lys Asn Thr Gln Pro Ile
385                 390                 395                 400

Met Asp Thr Asp Gly Ser Tyr Phe Val Tyr Ser Lys Leu Asn Val Gln
                405                 410                 415

Lys Ser Asn Trp Glu Ala Gly Asn Thr Phe Thr Cys Ser Val Leu His
            420                 425                 430

Glu Gly Leu His Asn His His Thr Glu Lys Ser Leu Ser His Ser Pro
        435                 440                 445

Gly Lys
    450

<210> SEQ ID NO 2
<211> LENGTH: 469
<212> TYPE: PRT
<213> ORGANISM: Artificial Sequence
<220> FEATURE:
<223> OTHER INFORMATION: Synthetic polypeptide

<400> SEQUENCE: 2

Met Glu Trp Ser Gly Val Phe Ile Phe Leu Leu Ser Val Thr Ala Gly
1               5                   10                  15

Ile His Ser Gln Val Gln Leu Gln Gln Ser Gly Ala Glu Leu Val Arg
            20                  25                  30

Pro Gly Thr Ser Val Lys Val Ser Cys Lys Ala Ser Gly Tyr Ala Phe
        35                  40                  45

```
Ile Asn Tyr Leu Ile Glu Trp Val Lys Gln Arg Pro Gly Gln Gly Leu
     50                  55                  60
Glu Trp Ile Gly Ile Ile Ser Pro Gly Ser Gly Ser Thr Asn Tyr Asn
 65                  70                  75                  80
Glu Glu Phe Arg Gly Arg Ala Thr Leu Thr Ala Asp Arg Ser Ser Ser
                 85                  90                  95
Thr Ala Tyr Met Gln Leu Ser Ser Leu Thr Ser Asp Asp Ser Ala Val
                100                 105                 110
Tyr Phe Cys Ala Arg Gly Gly Leu Thr His Tyr Ser Gly Ser Thr Tyr
            115                 120                 125
Glu Glu Gly Phe Asp Phe Trp Gly Gln Gly Thr Thr Leu Thr Val Ser
130                 135                 140
Ser Ala Lys Thr Thr Pro Pro Ser Val Tyr Pro Leu Ala Pro Gly Ser
145                 150                 155                 160
Ala Ala Gln Thr Asn Ser Met Val Thr Leu Gly Cys Leu Val Lys Gly
                165                 170                 175
Tyr Phe Pro Glu Pro Val Thr Val Thr Trp Asn Ser Gly Ser Leu Ser
            180                 185                 190
Ser Gly Val His Thr Phe Pro Ala Val Leu Gln Ser Asp Leu Tyr Thr
        195                 200                 205
Leu Ser Ser Ser Val Thr Val Pro Ser Ser Thr Trp Pro Ser Glu Thr
210                 215                 220
Val Thr Cys Asn Val Ala His Pro Ala Ser Ser Thr Lys Val Asp Lys
225                 230                 235                 240
Lys Ile Val Pro Arg Asp Cys Gly Cys Lys Pro Cys Ile Cys Thr Val
                245                 250                 255
Pro Glu Val Ser Ser Val Phe Ile Phe Pro Pro Lys Pro Lys Asp Val
            260                 265                 270
Leu Thr Ile Thr Leu Thr Pro Lys Val Thr Cys Val Val Val Asp Ile
        275                 280                 285
Ser Lys Asp Asp Pro Glu Val Gln Phe Ser Trp Phe Val Asp Asp Val
290                 295                 300
Glu Val His Thr Ala Gln Thr Gln Pro Arg Glu Glu Gln Phe Asn Ser
305                 310                 315                 320
Thr Phe Arg Ser Val Ser Glu Leu Pro Ile Met His Gln Asp Trp Leu
                325                 330                 335
Asn Gly Lys Glu Phe Lys Cys Arg Val Asn Ser Ala Ala Phe Pro Ala
            340                 345                 350
Pro Ile Glu Lys Thr Ile Ser Lys Thr Lys Gly Arg Pro Lys Ala Pro
        355                 360                 365
Gln Val Tyr Thr Ile Pro Pro Pro Lys Glu Gln Met Ala Lys Asp Lys
370                 375                 380
Val Ser Leu Thr Cys Met Ile Thr Asp Phe Phe Pro Glu Asp Ile Thr
385                 390                 395                 400
Val Glu Trp Gln Trp Asn Gly Gln Pro Ala Glu Asn Tyr Lys Asn Thr
                405                 410                 415
Gln Pro Ile Met Asp Thr Asp Gly Ser Tyr Phe Val Tyr Ser Lys Leu
            420                 425                 430
Asn Val Gln Lys Ser Asn Trp Glu Ala Gly Asn Thr Phe Thr Cys Ser
        435                 440                 445
Val Leu His Glu Gly Leu His Asn His His Thr Glu Lys Ser Leu Ser
450                 455                 460
```

His Ser Pro Gly Lys
            465

<210> SEQ ID NO 3
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 3

Asn Tyr Leu Ile Glu
1               5

<210> SEQ ID NO 4
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 4

Ile Ile Ser Pro Gly Ser Gly Ser Thr Asn Tyr Asn Glu Glu Phe Arg
1               5                   10                  15

Gly

<210> SEQ ID NO 5
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 5

Gly Gly Leu Thr His Tyr Ser Gly Ser Thr Tyr Glu Glu Gly Phe Asp
1               5                   10                  15

Phe

<210> SEQ ID NO 6
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 6

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Ile
            20                  25                  30

<210> SEQ ID NO 7
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 7

Trp Val Lys Gln Arg Pro Gly Gln Gly Leu Glu Trp Ile Gly
1               5                   10

<210> SEQ ID NO 8
<211> LENGTH: 32
<212> TYPE: PRT

```
<213> ORGANISM: Artificial Sequence
<220> FEATURE:
<223> OTHER INFORMATION: Synthetic polypeptide

<400> SEQUENCE: 8

Arg Ala Thr Leu Thr Ala Asp Arg Ser Ser Thr Ala Tyr Met Gln
1               5                   10                  15

Leu Ser Ser Leu Thr Ser Asp Asp Ser Ala Val Tyr Phe Cys Ala Arg
            20                  25                  30

<210> SEQ ID NO 9
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 9

Trp Gly Gln Gly Thr Thr Leu Thr Val Ser Ser
1               5                   10

<210> SEQ ID NO 10
<211> LENGTH: 126
<212> TYPE: PRT
<213> ORGANISM: Artificial Sequence
<220> FEATURE:
<223> OTHER INFORMATION: Synthetic polypeptide

<400> SEQUENCE: 10

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Ile Asn Tyr
            20                  25                  30

Leu Ile Glu Trp Val Lys Gln Arg Pro Gly Gln Gly Leu Glu Trp Ile
        35                  40                  45

Gly Ile Ile Ser Pro Gly Ser Gly Ser Thr Asn Tyr Asn Glu Glu Phe
    50                  55                  60

Arg Gly Arg Ala Thr Leu Thr Ala Asp Arg Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Gly Gly Leu Thr His Tyr Ser Gly Ser Thr Tyr Glu Glu Gly
            100                 105                 110

Phe Asp Phe Trp Gly Gln Gly Thr Thr Leu Thr Val Ser Ser
        115                 120                 125

<210> SEQ ID NO 11
<211> LENGTH: 324
<212> TYPE: PRT
<213> ORGANISM: Artificial Sequence
<220> FEATURE:
<223> OTHER INFORMATION: Synthetic polypeptide

<400> SEQUENCE: 11

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
```

```
            50                  55                  60
Ser Ser Ser Val Thr Val Pro Ser Ser Thr Trp Pro Ser Glu Thr Val
 65                  70                  75                  80

Thr Cys Asn Val Ala His Pro Ala Ser Ser Thr Lys Val Asp Lys Lys
                 85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
290                 295                 300

Leu His Glu Gly Leu His Asn His His Thr Glu Lys Ser Leu Ser His
305                 310                 315                 320

Ser Pro Gly Lys

<210> SEQ ID NO 12
<211> LENGTH: 215
<212> TYPE: PRT
<213> ORGANISM: Artificial Sequence
<220> FEATURE:
<223> OTHER INFORMATION: Synthetic polypeptide

<400> SEQUENCE: 12

Gln Ala Val Val Thr Gln Glu Ser Ala Leu Thr Thr Ser Pro Gly Glu
 1               5                  10                  15

Thr Val Thr Leu Thr Cys Arg Ser Ser Thr Gly Ala Val Thr Thr Thr
                20                  25                  30

Asn Tyr Ala Asn Trp Val Gln Glu Lys Pro Asp His Leu Phe Thr Gly
            35                  40                  45

Leu Ile Gly Gly Thr Asn Asn Arg Ala Pro Gly Val Pro Ala Arg Phe
        50                  55                  60

Ser Gly Ser Leu Ile Gly Asp Lys Ala Ala Leu Thr Ile Thr Gly Ala
 65                  70                  75                  80

Gln Thr Asp Asp Glu Ala Ile Tyr Phe Cys Ala Leu Trp Tyr Ser Asn
                 85                  90                  95
```

```
Arg Trp Val Phe Gly Gly Gly Thr Lys Leu Thr Val Leu Gly Gln Pro
                100                 105                 110

Lys Ser Ser Pro Ser Val Thr Leu Phe Pro Pro Ser Glu Glu Leu
            115                 120                 125

Glu Thr Asn Lys Ala Thr Leu Val Cys Thr Ile Thr Asp Phe Tyr Pro
130                 135                 140

Gly Val Val Thr Val Asp Trp Lys Val Asp Gly Thr Pro Val Thr Gln
145                 150                 155                 160

Gly Met Glu Thr Thr Gln Pro Ser Lys Gln Ser Asn Asn Lys Tyr Met
                165                 170                 175

Ala Ser Ser Tyr Leu Thr Leu Thr Ala Arg Ala Trp Glu Arg His Ser
            180                 185                 190

Ser Tyr Ser Cys Gln Val Thr His Glu Gly His Thr Val Glu Lys Ser
        195                 200                 205

Leu Ser Arg Ala Asp Cys Ser
    210                 215

<210> SEQ ID NO 13
<211> LENGTH: 234
<212> TYPE: PRT
<213> ORGANISM: Artificial Sequence
<220> FEATURE:
<223> OTHER INFORMATION: Synthetic polypeptide

<400> SEQUENCE: 13

Met Ala Trp Ile Ser Leu Ile Leu Ser Leu Leu Ala Leu Ser Ser Gly
1               5                   10                  15

Ala Ile Ser Gln Ala Val Val Thr Gln Glu Ser Ala Leu Thr Thr Ser
                20                  25                  30

Pro Gly Glu Thr Val Thr Leu Thr Cys Arg Ser Ser Thr Gly Ala Val
            35                  40                  45

Thr Thr Thr Asn Tyr Ala Asn Trp Val Gln Glu Lys Pro Asp His Leu
        50                  55                  60

Phe Thr Gly Leu Ile Gly Gly Thr Asn Asn Arg Ala Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Asp Asp Glu Ala Ile Tyr Phe Cys Ala Leu Trp
            100                 105                 110

Tyr Ser Asn Arg Trp Val Phe Gly Gly Gly Thr Lys Leu Thr Val Leu
        115                 120                 125

Gly Gln Pro Lys Ser Ser Pro Ser Val Thr Leu Phe Pro Pro Ser Ser
130                 135                 140

Glu Glu Leu Glu Thr Asn Lys Ala Thr Leu Val Cys Thr Ile Thr Asp
145                 150                 155                 160

Phe Tyr Pro Gly Val Val Thr Val Asp Trp Lys Val Asp Gly Thr Pro
                165                 170                 175

Val Thr Gln Gly Met Glu Thr Thr Gln Pro Ser Lys Gln Ser Asn Asn
            180                 185                 190

Lys Tyr Met Ala Ser Ser Tyr Leu Thr Leu Thr Ala Arg Ala Trp Glu
        195                 200                 205

Arg His Ser Ser Tyr Ser Cys Gln Val Thr His Glu Gly His Thr Val
    210                 215                 220

Glu Lys Ser Leu Ser Arg Ala Asp Cys Ser
225                 230
```

<210> SEQ ID NO 14
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 14

Arg Ser Ser Thr Gly Ala Val Thr Thr Thr Asn Tyr Ala Asn
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 15

Gly Thr Asn Asn Arg Ala Pro
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 16

Ala Leu Trp Tyr Ser Asn Arg Trp Val
1               5

<210> SEQ ID NO 17
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 17

Gln Ala Val Val Thr Gln Glu Ser Ala Leu Thr Thr Ser Pro Gly Glu
1               5                   10                  15

Thr Val Thr Leu Thr Cys
            20

<210> SEQ ID NO 18
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 18

Trp Val Gln Glu Lys Pro Asp His Leu Phe Thr Gly Leu Ile Gly
1               5                   10                  15

<210> SEQ ID NO 19
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 19

```
Gly Val Pro Ala Arg Phe Ser Gly Ser Leu Ile Gly Asp Lys Ala Ala
1               5                   10                  15

Leu Thr Ile Thr Gly Ala Gln Thr Asp Asp Glu Ala Ile Tyr Phe Cys
            20                  25                  30
```

<210> SEQ ID NO 20
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 20

```
Phe Gly Gly Gly Thr Lys Leu Thr Val Leu
1               5                   10
```

<210> SEQ ID NO 21
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 21

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Thr
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Asp Asp Glu Ala Ile Tyr Phe Cys Ala Leu Trp Tyr Ser Asn
                85                  90                  95

Arg Trp Val Phe Gly Gly Gly Thr Lys Leu Thr Val Leu
            100                 105
```

<210> SEQ ID NO 22
<211> LENGTH: 106
<212> TYPE: PRT
<213> ORGANISM: Artificial Sequence
<220> FEATURE:
<223> OTHER INFORMATION: Synthetic polypeptide

<400> SEQUENCE: 22

```
Gly Gln Pro Lys Ser Ser Pro Ser Val Thr Leu Phe Pro Pro Ser Ser
1               5                   10                  15

Glu Glu Leu Glu Thr Asn Lys Ala Thr Leu Val Cys Thr Ile Thr Asp
            20                  25                  30

Phe Tyr Pro Gly Val Val Thr Val Asp Trp Lys Val Asp Gly Thr Pro
        35                  40                  45

Val Thr Gln Gly Met Glu Thr Thr Gln Pro Ser Lys Gln Ser Asn Asn
    50                  55                  60

Lys Tyr Met Ala Ser Ser Tyr Leu Thr Leu Thr Ala Arg Ala Trp Glu
65                  70                  75                  80

Arg His Ser Ser Tyr Ser Cys Gln Val Thr His Glu Gly His Thr Val
                85                  90                  95

Glu Lys Ser Leu Ser Arg Ala Asp Cys Ser
            100                 105
```

<210> SEQ ID NO 23
<211> LENGTH: 1350
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1350)
<223> OTHER INFORMATION: This sequence may include a stop sequence, such as TGA

<400> SEQUENCE: 23

```
caggtccaac tgcagcagtc tggagctgaa ctggtaaggc cggggacttc agtgaaggtg      60
tcctgcaagg cttctggata cgccttcatt aattacttga tagaatgggt gaaacagagg     120
cctggacagg gccttgagtg gattggaata ataagtcctg aagtggtag  tactaactac     180
aatgaagagt tcaggggcag ggcaacactg actgcagaca gatcctccag cactgcctac     240
atgcagctca gcagcctgac atctgatgac tctgcggtct atttctgtgc aagagggggc     300
ttaactcatt actccggcag tacgtacgaa gagggctttg acttctgggg ccaaggcacc     360
actctcacag tctcctcagc caaaacgaca cccccatctg tctatccact ggcccctgga     420
tctgctgccc aaactaactc catggtgacc ctgggatgcc tggtcaaggg ctatttccct     480
gagccagtga cagtgacctg aactctggat ccctgtcca gcggtgtgca caccttccca     540
gctgtcctgc agtctgacct ctacactctg agcagctcag tgactgtccc ctccagcacc     600
tggcccagcg agaccgtcac ctgcaacgtt gcccacccgg ccagcagcac caaggtggac     660
aagaaaattg tgcccaggga ttgtggttgt aagccttgca tatgtacagt cccagaagta     720
tcatctgtct tcatcttccc cccaaagccc aaggatgtgc tcaccattac tctgactcct     780
aaggtcacgt gtgttgtggt agacatcagc aaggatgatc ccgaggtcca gttcagctgg     840
tttgtagatg atgtggaggt gcacacagct cagacgcaac cccgggagga gcagttcaac     900
agcactttcc gctcagtcag tgaacttccc atcatgcacc aggactggct caatggcaag     960
gagttcaaat gcagggtcaa cagtgcagct ttccctgccc ccatcgagaa aaccatctcc    1020
aaaaccaaag gcagaccgaa ggctccacag gtgtacacca ttccacctcc caaggagcag    1080
atggccaagg ataaagtcag tctgacctgc atgataacac acttcttccc tgaagacatt    1140
actgtggagt ggcagtggaa tgggcagcca gcggagaact acaagaacac tcagcccatc    1200
atggacacag atggctctta cttcgtctac agcaagctca atgtgcagaa gagcaactgg    1260
gaggcaggaa atactttcac ctgctctgtg ttacatgagg gcctgcacaa ccaccatact    1320
gagaagagcc tctcccactc tcctggtaaa                                     1350
```

<210> SEQ ID NO 24
<211> LENGTH: 1407
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1407)
<223> OTHER INFORMATION: This sequence may include a stop sequence, such as TGA

<400> SEQUENCE: 24

```
atggaatgga gcggagtctt tatctttctc ctgtcagtaa ctgcaggtat tcactcccag      60
```

```
gtccaactgc agcagtctgg agctgaactg gtaaggccgg ggacttcagt gaaggtgtcc    120
tgcaaggctt ctggatacgc cttcattaat tacttgataa aatgggtgaa acagaggcct    180
ggacagggcc ttgagtggat tggaataata agtcctggaa gtggtagtac taactacaat    240
gaagagttca gggcagggc aacactgact gcagacagat cctccagcac tgcctacatg    300
cagctcagca gcctgacatc tgatgactct gcggtctatt tctgtgcaag agggggctta    360
actcattact ccggcagtac gtacgaagag gctttgact tctggggcca aggcaccact    420
ctcacagtct cctcagccaa aacgacaccc ccatctgtct atccactggc ccctggatct    480
gctgcccaaa ctaactccat ggtgaccctg ggatgcctgg tcaagggcta tttccctgag    540
ccagtgacag tgacctggaa ctctggatcc ctgtccagcg gtgtgcacac cttcccagct    600
gtcctgcagt ctgacctcta cactctgagc agctcagtga ctgtcccctc cagcacctgg    660
cccagcgaga ccgtcacctg caacgttgcc cacccggcca gcagcaccaa ggtggacaag    720
aaaattgtgc ccagggattg tggttgtaag ccttgcatat gtacagtccc agaagtatca    780
tctgtcttca tcttcccccc aaagcccaag gatgtgctca ccattactct gactcctaag    840
gtcacgtgtg ttgtggtaga catcagcaag gatgatcccg aggtccagtt cagctggttt    900
gtagatgatg tggaggtgca cacagctcag acgcaacccc gggaggagca gttcaacagc    960
actttccgct cagtcagtga acttcccatc atgcaccagg actggctcaa tggcaaggag   1020
ttcaaatgca gggtcaacag tgcagctttc cctgccccca tcgagaaaac catctccaaa   1080
accaaaggca gaccgaaggc tccacaggtg tacaccattc cacctcccaa ggagcagatg   1140
gccaaggata agtcagtctg acctgcatg ataacagact tcttccctga agacattact   1200
gtggagtggc agtggaatgg gcagccagcg gagaactaca agaacactca gcccatcatg   1260
gacacagatg gctcttactt cgtctacagc aagctcaatg tgcagaagag caactgggag   1320
gcaggaaata ctttcacctg ctctgtgtta catgagggcc tgcacaacca ccatactgag   1380
aagagcctct cccactctcc tggtaaa                                       1407
```

<210> SEQ ID NO 25
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 25

```
aattacttga tagaa                                                      15
```

<210> SEQ ID NO 26
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 26

```
ataataagtc ctggaagtgg tagtactaac tacaatgaag agttcagggg c              51
```

<210> SEQ ID NO 27
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 27 ggggcttaa ctcattactc cggcagtacg tacgaagagg ctttgactt c        51

<210> SEQ ID NO 28
<211> LENGTH: 90
<212> TYPE: DNA
<213> ORGANISM: Artificial Sequence
<220> FEATURE:
<223> OTHER INFORMATION: Synthetic polynucleotide

<400> SEQUENCE: 28
caggtccaac tgcagcagtc tggagctgaa ctggtaaggc cggggacttc agtgaaggtg        60
tcctgcaagg cttctggata cgccttcatt        90

<210> SEQ ID NO 29
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 29
tgggtgaaac agaggcctgg acagggcctt gagtggattg ga        42

<210> SEQ ID NO 30
<211> LENGTH: 96
<212> TYPE: DNA
<213> ORGANISM: Artificial Sequence
<220> FEATURE:
<223> OTHER INFORMATION: Synthetic polynucleotide

<400> SEQUENCE: 30
agggcaacac tgactgcaga cagatcctcc agcactgcct acatgcagct cagcagcctg        60
acatctgatg actctgcggt ctatttctgt gcaaga        96

<210> SEQ ID NO 31
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 31
tggggccaag gcaccactct cacagtctcc tca        33

<210> SEQ ID NO 32
<211> LENGTH: 378
<212> TYPE: DNA
<213> ORGANISM: Artificial Sequence
<220> FEATURE:
<223> OTHER INFORMATION: Synthetic polynucleotide

<400> SEQUENCE: 32
caggtccaac tgcagcagtc tggagctgaa ctggtaaggc cggggacttc agtgaaggtg        60
tcctgcaagg cttctggata cgccttcatt aattacttga tagaatgggt gaaacagagg       120
cctggacagg gccttgagtg gattggaata ataagtcctg gaagtggtag tactaactac       180
aatgaagagt tcaggggcag ggcaacactg actgcagaca gatcctccag cactgcctac       240
atgcagctca gcagcctgac atctgatgac tctgcggtct atttctgtgc aagagggggc       300
ttaactcatt actccggcag tacgtacgaa gagggctttg acttctgggg ccaaggcacc       360
actctcacag tctcctca        378

<210> SEQ ID NO 33
<211> LENGTH: 972
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(972)
<223> OTHER INFORMATION: This sequence may include a stop sequence, such as TGA

<400> SEQUENCE: 33

```
gccaaaacga cacccccatc tgtctatcca ctggcccctg gatctgctgc ccaaactaac     60
tccatggtga ccctgggatg cctggtcaag ggctatttcc ctgagccagt gacagtgacc    120
tggaactctg gatccctgtc cagcggtgtg cacaccttcc cagctgtcct gcagtctgac    180
ctctacactc tgagcagctc agtgactgtc ccctccagca cctggcccag cgagaccgtc    240
acctgcaacg ttgcccaccc ggccagcagc accaaggtgg acaagaaaat tgtgcccagg    300
gattgtggtt gtaagccttg catatgtaca gtcccagaag tatcatctgt cttcatcttc    360
cccccaaagc ccaaggatgt gctcaccatt actctgactc ctaaggtcac gtgtgttgtg    420
gtagacatca gcaaggatga tcccgaggtc cagttcagct ggtttgtaga tgatgtggag    480
gtgcacacag ctcagacgca accccgggag gagcagttca acagcacttt ccgctcagtc    540
agtgaacttc ccatcatgca ccaggactgg ctcaatggca aggagttcaa atgcagggtc    600
aacagtgcag ctttccctgc ccccatcgag aaaaccatct ccaaaaccaa aggcagaccg    660
aaggctccac aggtgtacac cattccacct cccaaggagc agatggccaa ggataaagtc    720
agtctgacct gcatgataac agacttcttc cctgaagaca ttactgtgga gtggcagtgg    780
aatgggcagc cagcggagaa ctacaagaac actcagccca tcatggacac agatggctct    840
tacttcgtct acagcaagct caatgtgcag aagagcaact gggaggcagg aaatactttc    900
acctgctctg tgttacatga gggcctgcac aaccaccata ctgagaagag cctctcccac    960
tctcctggta aa                                                        972
```

<210> SEQ ID NO 34
<211> LENGTH: 645
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(645)
<223> OTHER INFORMATION: This sequence may include a stop sequence, such as TGA

<400> SEQUENCE: 34

```
caggctgttg tgactcagga atctgcactc accacatcac ctggtgaaac agtcacactc     60
acttgtcgct caagtactgg ggctgttaca actactaact atgccaactg gtccaagaa    120 aaaccagatc atttattcac tggtctaata ggtggtacca acaaccgagc tccaggtgtt    180
cctgccagat tctcaggctc cctgattgga gacaaggctg ccctcaccat cacagggca    240 cagactgatg atgaggcaat atatttctgt gctctatggt acagcaaccg ctgggtgttc    300
ggtggaggaa ccaaactgac tgtcctaggc cagcccaagt cttcgccatc agtcaccctg    360
tttccacctt cctctgaaga gctcgagact aacaaggcca cactggtgtg tacgatcact    420
```

```
gatttctacc caggtgtggt gacagtggac tggaaggtag atggtacccc tgtcactcag    480
ggtatggaga caacccagcc ttccaaacag agcaacaaca agtacatggc tagcagctac    540
ctgaccctga cagcaagagc atgggaaagg catagcagtt acagctgcca ggtcactcat    600
gaaggtcaca ctgtggagaa gagtttgtcc cgtgctgact gttcc                    645
```

<210> SEQ ID NO 35
<211> LENGTH: 702
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(702)
<223> OTHER INFORMATION: This sequence may include a stop sequence, such as TGA

<400> SEQUENCE: 35

```
atggcctgga tttcacttat actctctctc ctggctctca gctcagggac catttcccag    60
gctgttgtga ctcaggaatc tgcactcacc acatcacctg gtgaaacagt cacactcact    120
tgtcgctcaa gtactggggc tgttacaact actaactatg ccaactgggt ccaagaaaaa    180
ccagatcatt tattcactgg tctaataggt ggtaccaaca accgagctcc aggtgttcct    240
gccagattct caggctccct gattggagac aaggctgccc tcaccatcac aggggcacag    300
actgatgatg aggcaatata tttctgtgct ctatggtaca gcaaccgctg gtgttcggt     360 ggaggaacca aactgactgt cctaggccag cccaagtctt cgccatcagt caccctgttt    420
ccaccttcct ctgaagagct cgagactaac aaggccacac tggtgtgtac gatcactgat    480
ttctacccag gtgtggtgac agtggactgg aaggtagatg gtaccccttgt cactcagggt    540 atggagacaa cccagccttc caaacagagc aacaacaagt acatggctag cagctacctg    600
accctgacag caagagcatg ggaaaggcat agcagttaca gctgccaggt cactcatgaa    660
ggtcacactg tggagaagag tttgtcccgt gctgactgtt cc                       702
```

<210> SEQ ID NO 36
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 36

```
cgctcaagta ctggggctgt tacaactact aactatgcca ac                       42
```

<210> SEQ ID NO 37
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 37

```
ggtaccaaca accgagctcc a                                              21
```

<210> SEQ ID NO 38
<211> LENGTH: 27
<212> TYPE: DNA
<213> ORGANISM: Artificial Sequence
<220> FEATURE:
<223> OTHER INFORMATION: Synthetic polynucleotide

```
<400> SEQUENCE: 38
gctctatggt acagcaaccg ctgggtg                                        27

<210> SEQ ID NO 39
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 39
caggctgttg tgactcagga atctgcactc accacatcac ctggtgaaac agtcacactc    60
acttgt                                                               66

<210> SEQ ID NO 40
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 40
tgggtccaag aaaaaccaga tcatttattc actggtctaa taggt                    45

<210> SEQ ID NO 41
<211> LENGTH: 96
<212> TYPE: DNA
<213> ORGANISM: Artificial Sequence
<220> FEATURE:
<223> OTHER INFORMATION: Synthetic polynucleotide

<400> SEQUENCE: 41
ggtgttcctg ccagattctc aggctccctg attggagaca aggctgccct caccatcaca    60
ggggcacaga ctgatgatga ggcaatatat ttctgt                              96

<210> SEQ ID NO 42
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 42
ttcggtggag gaaccaaact gactgtccta                                     30

<210> SEQ ID NO 43
<211> LENGTH: 327
<212> TYPE: DNA
<213> ORGANISM: Artificial Sequence
<220> FEATURE:
<223> OTHER INFORMATION: Synthetic polynucleotide

<400> SEQUENCE: 43
caggctgttg tgactcagga atctgcactc accacatcac ctggtgaaac agtcacactc    60
acttgtcgct caagtactgg ggctgttaca actactaact atgccaactg gtccaagaa    120 aaaccagatc atttattcac tggtctaata ggtggtacca caaccgagc tccaggtgtt   180 cctgccagat tctcaggctc cctgattgga gacaaggctg ccctcaccat cacaggggca   240
cagactgatg atgaggcaat atatttctgt gctctatggt acagcaaccg ctgggtgttc   300
ggtggaggaa ccaaactgac tgtccta                                       327
```

```
<210> SEQ ID NO 44
<211> LENGTH: 318
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(318)
<223> OTHER INFORMATION: This sequence may include a stop sequence, such
      as TGA

<400> SEQUENCE: 44
ggccagccca agtcttcgcc atcagtcacc ctgtttccac cttcctctga agagctcgag      60
actaacaagg ccacactggt gtgtacgatc actgatttct acccaggtgt ggtgacagtg     120
gactggaagg tagatggtac ccctgtcact cagggtatgg agacaaccca gccttccaaa     180
cagagcaaca acaagtacat ggctagcagc tacctgaccc tgcagcaag agcatgggaa      240 aggcatagca gttacagctg ccaggtcact catgaaggtc acactgtgga gaagagtttg     300
tcccgtgctg actgttcc                                                    318

<210> SEQ ID NO 45
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 45

Cys Gln Leu Ser Asn Arg Phe Pro Arg Tyr Asn Asn Pro Glu Lys Leu
1               5                   10                  15

Leu

<210> SEQ ID NO 46
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 46

Ile Ser Pro Lys Thr Pro Arg Pro Gly Glu Leu Gly Gly Arg Val Ser
1               5                   10                  15

Gly Ser Leu
```

ANTI-NGLY-1 ANTIBODIES AND METHODS OF USE

RELATED APPLICATIONS

This application is a national stage filing under 35 U.S.C. § 371 of International Patent Application Serial No. PCT/US2019/033499, filed May 22, 2019, which was published under PCT Article 21(2) in English and claims the benefit under 35 U.S.C. § 119(e) of U.S. provisional application No. 62/675,715, filed May 23, 2018, and U.S. provisional application No. 62/697,058, filed Jul. 12, 2018, each of which is incorporated by reference herein in its entirety.

REFERENCE TO AN ELECTRONIC SEQUENCE LISTING

The content of the electronic sequence listing (J022770013US02-SEQ-JXV.txt; Size: 35,813 bytes; and Date of Creation: Nov. 20, 2020) is herein incorporated by reference in its entirety.

BACKGROUND

The Ngly1R539X allele has a one (1) base pair replacement in the mouse N-glycanase 1 (NGly-1) gene that encodes a nonsense mutation, resulting in a premature stop codon. This mutation corresponds to the R524X mutation identified in the patient population as a disease causing variant in Congenital Disorders of Glycosylation Type IV, also referred to as Alacrimia-Choreoathetosis-Liver Dysfunction Syndrome and NGLY1 deficiency.

SUMMARY

Provide herein, in some embodiments, is an antibody that binds specifically to mouse NGly-1 and human NGLY-1. In some embodiments, the antibody comprises a heavy chain comprising, (a) a CDR1 comprising the sequence of SEQ ID NO: 3, (b) a CDR2 comprising the sequence of SEQ ID NO: 4, and (c) a CDR3 comprising the sequence of SEQ ID NO: 5. In some embodiments, the anti-NGly-1 antibody comprises a light chain comprising, (a) a CDR 1 comprising the sequence of SEQ ID NO: 14, (b) a CDR2 comprising the sequence of SEQ ID NO: 15, and (c) a CDR3 comprising the sequence of SEQ ID NO: 16.

Also provided herein are compositions and kits comprising an antibody that binds specifically to NGly-1 and NGLY-1.

Further provided herein are methods that include contacting a cell with an antibody that binds specifically to NGly-1 and NGLY-1. Such methods may be used, for example, to diagnose a subject with NGLY1 deficiency. Diagnostic kits comprising the antibodies described herein are also provided.

Also provided herein are methods for using an antibody that binds specifically to NGly-1 and NGLY-1 for the treatment of a cancer.

The antibodies provided herein can bind specifically to either human NGLY-1 protein or mouse NGly-1 protein. For simplicity, it should be understood that reference to an "antibody that binds to specifically NGly-1" or an "anti-Ngly-1 antibody" encompasses antibodies that can bind specifically to mouse NGly-1 protein and can bind specifically to human NGLY-1 protein.

BRIEF DESCRIPTION OF THE DRAWINGS

FIG. 8B: Lane 1: JR00664 Brain Total extract; v2: JR 00664 Brain Mitochondrial fraction; Lane 3: JR 00664 Brain Cytosolic Fraction; Lane 4: JR00664 Liver Total extract; Lane 5: JR 27962 (Het)

Liver Total extract; Lane 6: JR 00664 Liver Mitochondrial Fraction; Lane 7: JR 00664 Liver cytosolic fraction; Lane 8: NIH3T3 cell line (mouse).

Figure 9:
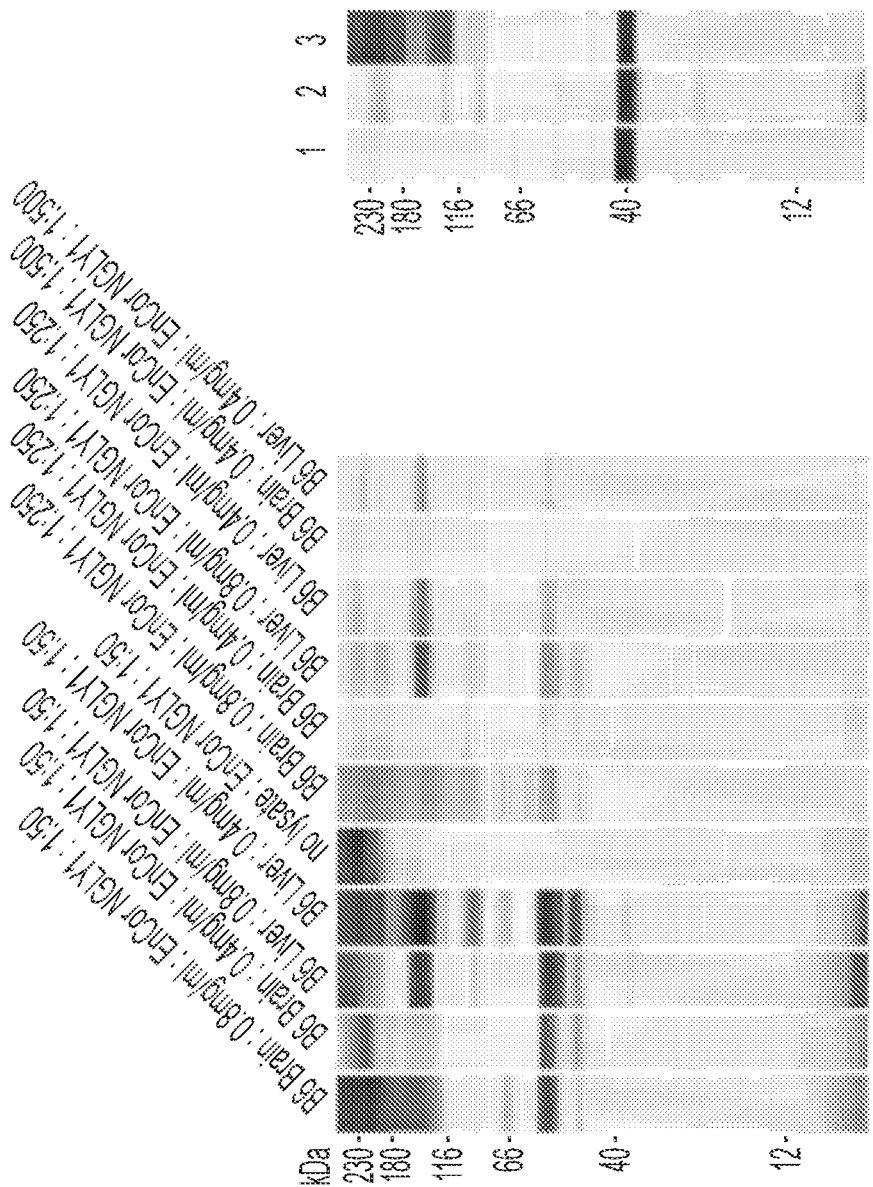

FIG. 9 shows data demonstrating that yet another commercially-available anti-NGlyc-1 antibody (ENCOR) produces a high background, and the predominant protein detected is significantly smaller than expected. Screening the antibody against lysates from known Ngly-1 protein null strains revealed multiple bands remaining. Thus, this commercially-available antibody is non-specific. The antibody was made against the N-terminal 300 amino acids of Human NGLY-1. Lane 1: JR00664 C57BL/6J E16.5 embryo Brain; Lane 2: JR27060 Ngly1 null mouse E16.5 embryo Brain; Lane 3: JR28975 Ngly1 null mouse E16.5 embryo Brain.

DETAILED DESCRIPTION

NGLY1 deficiency is a rare inherited disorder that affects children lacking NGLY1 normal expression or function. These children demonstrate global development delay, loss of muscle tone, peripheral neuropathy, seizures, poor reflexes, speech impairment, lack of tear production, corneal scarring, chronic constipation and/or liver dysfunction. The protein product of NGLY1 encodes an enzyme called N-glycanase 1, also known as PNGase, which catalyzes the removal of N-linked oligosaccharides from the asparagine side chains of glycoproteins. Cytoplasmic PNGase activity was first reported in *Saccharomyces cerevisiae* (Suzuki et al 2000), but subsequently found to be evolutionarily conserved in many species including *Drosophila, C. elegans*, mouse and human.

Some aspects of the present disclosure provide an antibody that binds specifically to NGly-1 and comprises a heavy chain and a light chain, wherein the heavy chain comprises (a) a CDR1 comprising the sequence of SEQ ID NO: 3, (b) a CDR2 comprising the sequence of SEQ ID NO: 4, and (c) a CDR3 comprising the sequence of SEQ ID NO: 5, and/or the light chain comprises (a) a CDR1 comprising the sequence of SEQ ID NO: 14, (b) a CDR2 comprising the sequence of SEQ ID NO: 15, and (c) a CDR3 comprising the sequence of SEQ ID NO: 16.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) monoclonal antibodies, but also antigen-binding fragments (such as Fab, Fab', F(ab')2, Fv), single chain variable fragment (scFv), mutants thereof, fusion proteins comprising an antibody portion, humanized antibodies, chimeric antibodies, diabodies, linear antibodies, single chain antibodies, single domain antibodies (e.g., camel or llama VHH antibodies), multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibodies to be used in the methods described herein can be murine, rat, human, or any other origin (including chimeric or humanized antibodies). In some examples, the antibody comprises a modified constant region, such as a constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613-2624; PCT Application No. PCT/GB99/01441; and/or UK Patent Application No. 9809951.8.

In some embodiments, an antibody of the present disclosure is a monoclonal antibody. A "monoclonal antibody" refers to a homogenous antibody population.

In some embodiments, an antibody of the present disclosure is a humanized antibody. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. A humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In other embodiments, an antibody of the present disclosure is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, an antibody of the present disclosure specifically binds a target antigen, such as (mouse or human) NGly-1. An antibody that "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically (or preferentially) binds to an NGly-1 epitope is an antibody that binds this NGly-1 epitope with greater affinity, avidity, more readily, and/or with greater duration than it binds to other NGly-1 epitopes or non-NGly-1 epitopes. In some embodiments, the NGly-1 epitope comprises SEQ ID NO: 45 or 46. In some embodiments, the disclosure provides a peptide comprising or consisting of the amino acid sequence of SEQ ID NO: 45. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

In some embodiments, the equilibrium dissociation constant ($K_D$) between the antibody and NGly-1 is 100 pM to 1000 pM. For example, the $K_D$ between the antibody and NGly-1 may be 100 pM to 900 pM, 100 pM to 800 pM, 100 pM to 700 pM, 100 pM to 600 pM, 100 pM to 500 pM, 100 pM to 400 pM, 100 pM to 300 pM, 150 pM to 1000 pM, 150 pM to 900 pM, 150 pM to 800 pM, 150 pM to 700 pM, 150 pM to 600 pM, 150 pM to 500 pM, 150 pM to 400 pM, 150 pM to 300 pM, 200 pM to 1000 pM, 200 pM to 900 pM, 200 pM to 800 pM, 200 pM to 700 pM, 200 pM to 600 pM, 200 pM to 500 pM, 200 pM to 400 pM, 200 pM to 300 pM, 250 pM to 1000 pM, 250 pM to 900 pM, 250 pM to 800 pM, 250 pM to 700 pM, 250 pM to 600 pM, 250 pM to 500 pM, 250 pM to 400 pM, or 250 pM to 300 pM. In some embodiments, the equilibrium dissociation constant ($K_D$) between the antibody and NGly-1 is 100 pM, 150 pM, 200 pM, 210 pM, 220 pM, 230 PM, 240 pM, 250 pM, 260 pM, 270 pM, 280 pM, 290 pM, or 300 pM. In some embodiments, the equilibrium dissociation constant ($K_D$) between the antibody and NGly-1 is less than 500 pM, less than 400 pM, or less than 300 pM. In some embodiments, the $K_D$ between the antibody and NGly-1 is 1 nM to 100 nM.

Heavy Chain

A heavy chain is the large polypeptide subunit of an antibody. Heavy chains differ in size and composition, but are typically between 450 and 550 amino acids in length and are composed of a constant domain (HC Constant), comprising three or four immunoglobulin domains, and a variable domain (HC Variable), comprising a single immunoglobulin domain. The variable domain of the heavy chain is important for binding antigen. An immunoglobulin domain is a structure formed by the three-dimensional arrangement of beta-strands into parallel beta-sheets. There are five types of heavy chains in mammals which define the class of antibody, wherein IgA antibodies contain alpha (α) heavy chains, IgD antibodies contain delta (δ) heavy chains, IgE antibodies contain epsilon (ε) heavy chains, IgM antibodies contain mu (μ) heavy chains, and IgG antibodies contain gamma (γ) heavy chains.

In some embodiments, the heavy chain of an antibody of the present disclosure comprises the sequence of SEQ ID NO: 1. In some embodiments, the heavy chain of an antibody of the present disclosure comprises a sequences that has at least 95%, 96%, 97%, 98%, or 99% identity to the sequence of SEQ ID NO: 1.

Light Chain

A light chain is the small polypeptide of an antibody. Light chains differ in size, but are typically between 210 and 217 amino acids in length and are composed of a constant domain (LC Constant), comprising a single immunoglobulin domain, and a variable domain (LC Variable), comprising a single immunoglobulin domain. There are two types of light chains in mammals, which are defined by the sequence of the constant region and classified as either kappa (κ) or lambda (λ). The variable domain of the light chain is important for binding antigen. Only one type of light chain is typically present in an antibody, so the two light chains within a single antibody are identical.

In some embodiments, the light chain of an antibody of the present disclosure comprises the sequence of SEQ ID NO: 13. In some embodiments, the light chain of an antibody of the present disclosure comprises a sequences that has at least 95%, 96%, 97%, 98%, or 99% identity to the sequence of SEQ ID NO: 13.

Variable Region

Each antibody has a unique variable region composed of the variable domains of both heavy and light chains which contains the antigen binding site. The variable region is further subdivided into complementarity determining regions (CDRs) and framework (FR) regions. There are two variable domains on each antibody which typically, but not always, bind the same antigen.

In some embodiments, the heavy chain comprises a variable region that is at least 90% or at least 95% (e.g., at least 96%, 97%, 98%, or 99%) identical to the sequence of SEQ ID NO: 10. In some embodiments, the heavy chain comprises a variable region that comprises the sequence of SEQ ID NO: 10.

In some embodiments, the light chain comprises a variable region that is at least 90% or at least 95% (e.g., at least 96%, 97%, 98%, or 99%) identical to the sequence of SEQ ID NO: 21. In some embodiments, the light chain comprises a variable region that comprises the sequence of SEQ ID NO: 21.

CDR

A complementarity-determining region (CDR) (also known as a hypervariable region, or HV) within the variable region has a high ratio of different amino acids in a given position, relative to the most common amino acid in that position. Three CDRs (CDR1, CDR2, CDR3) exist within heavy and light chains, which form flexible loops that directly contact a portion of the antigen's surface.

In some embodiments, an antibody that binds specifically to NGly-1 comprises a heavy chain comprising (a) a CDR1 comprising the sequence of SEQ ID NO: 3, (b) a CDR2 comprising the sequence of SEQ ID NO: 4, and (c) a CDR3 comprising the sequence of SEQ ID NO: 5.

In some embodiments, an antibody that binds specifically to NGly-1 comprises a light chain comprising (a) a CDR1 comprising the sequence of SEQ ID NO: 14, (b) a CDR2 comprising the sequence of SEQ ID NO: 15, and (c) a CDR3 comprising the sequence of SEQ ID NO: 16.

Framework Region

The framework region (FR) within a variable region is composed of conserved amino acid sequences which separate CDR sequences. The FR regions form a beta-sheet structure which serves as a scaffold to hold the CDRs in position to contact the antigen surface. Four FR regions exist within each heavy and light chain.

In some embodiments, the heavy chain comprises a framework region that is at least 90% or at least 95% (e.g., at least 96%, 97%, 98%, or 99%) identical to the sequence of SEQ ID NO: 6; a framework region that is at least 90% or at least 95% (e.g., at least 96%, 97%, 98%, or 99%) identical to the sequence of SEQ ID NO: 7; a framework region that is at least 90% or at least 95% identical to the sequence of SEQ ID NO: 8; and/or a framework region that is at least 90% or at least 95% (e.g., at least 96%, 97%, 98%, or 99%) identical to the sequence of SEQ ID NO:9.

In some embodiments, the light chain comprises a framework region that is at least 90% (e.g., at least 91%, 92%, 93%, 94%, 95%, 96%, 97%, 98%, or 99%) identical to the sequence of SEQ ID NO: 17; a framework region that is at least 90% (e.g., at least 91%, 92%, 93%, 94%, 95%, 96%, 97%, 98%, or 99%) identical to the sequence of SEQ ID NO: 18; a framework region that is at least 90% (e.g., at least 91%, 92%, 93%, 94%, 95%, 96%, 97%, 98%, or 99%) identical to the sequence of SEQ ID NO: 19; and/or a framework region that is at least 90% (e.g., at least 91%, 92%, 93%, 94%, 95%, 96%, 97%, 98%, or 99%) identical to the sequence of SEQ ID NO: 20.

Constant Region

The constant region of an antibody is recognized by receptors on immune cells and proteins to initiate and regulate host defense mechanisms. The constant region of heavy chain polypeptides is identical in all antibodies of the immunoglobulin class, but differs between immunoglobulin classes. Heavy chains in Igγ, Igα, and Igδ contain a constant region composed of three immunoglobulin domains and a hinge region for increased flexibility. Heavy chains in Igμ and Igε contain a constant region composed of four immunoglobulin domains. The constant region of light chain polypeptides is composed of a single immunoglobulin domain.

In some embodiments, a heavy chain comprises a constant region that is at least 90% or at least 95% (e.g., at least 96%, 97%, 98%, or 99%) identical to the sequence of SEQ ID NO: 11. In some embodiments, a heavy chain comprises a constant region that comprises the sequence of SEQ ID NO: 11.

In some embodiments, the light chain comprises a constant region that is at least 90% or at least 95% (e.g., at least 96%, 97%, 98%, or 99%) identical to the sequence of SEQ ID NO: 22. In some embodiments, a light chain comprises a constant region that comprises the sequence of SEQ ID NO: 22.

Polynucleotides and Antibody Synthesis

The present disclosure also provides polynucleotides encoding the antibody described herein. "Polynucleotide," as used herein, includes both a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. An "isolated" polynucleotide is, for example, DNA or RNA that has been removed from its native environment. For example, a recombinant polynucleotide encoding an antibody contained in a vector is considered isolated for the purposes of the present disclosure. Further examples of isolated polynucleotides include recombinant polynucleotides maintained in heterologous host cells or purified (partially or substantially) polynucleotides in solution. Isolated RNA molecules include in vivo or in vitro RNA transcripts of polynucleotides of the present disclosure. Isolated polynucleotides or nucleic acids may further include such molecules produced synthetically. In addition, a polynucleotide may include a regulatory element such as a promoter, ribosome binding site, or a transcription terminator. Exemplary polynucleotide sequences are provided in Table 2 (SEQ ID NOs: 23-44).

Following synthesis of the polynucleotide encoding the antibody, the polynucleotide may be inserted in an expression vector for introduction into host cells that may be used to produce the desired antibody. Recombinant expression of an antibody, or fragment thereof, e.g., a heavy or light chain of an antibody is described herein. Once a polynucleotide encoding an antibody molecule or a heavy or light chain of an antibody, or portion thereof (preferably containing the heavy or light chain variable domain), has been obtained, the vector for the production of the antibody molecule may be produced by recombinant DNA technology using techniques available in the art. Thus, methods for preparing a protein by expressing a polynucleotide containing an antibody encoding nucleotide sequence are described herein. Methods that are available to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The disclosure therefore provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule, and the variable domain of the antibody may be cloned into such a vector for expression of the entire heavy or light chain.

The term "vector" or "expression vector" is used herein to refer to a vehicle for introducing into and expressing a desired gene in a host cell. Vectors may be selected from the group consisting of plasmids, phages, viruses and retroviruses. In some embodiments, vectors comprise a selection marker, appropriate restriction sites to facilitate cloning of the desired gene, and the ability to enter and/or replicate in eukaryotic or prokaryotic cells. Numerous expression vector systems may be employed in accordance with the disclosure.

Once the vector or DNA sequence encoding a monomeric subunit of the antibody has been prepared, the expression vector may be introduced into an appropriate host cell. Introduction of the plasmid into the host cell can be accomplished by various techniques available to those of skill in the art. These include, but are not limited to, transfection including lipotransfection using, e.g., Fugene® or lipofectamine, protoplast fusion, calcium phosphate precipitation, cell fusion with enveloped DNA, microinjection, and infection with intact virus. In some embodiments, plasmid introduction into the host is via standard calcium phosphate co-precipitation method. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), and immunohistochemistry.

The expression vector may be transferred to a host cell by any available cell-transfection technique. The transfected cells may then be cultured by available techniques to produce an antibody described herein. Thus, the disclosure provides host cells containing a polynucleotide encoding an antibody of the present disclosure, or a heavy or light chain thereof, in some embodiments, operably linked to a heterologous promoter.

Once an antibody molecule described herein has been recombinantly expressed, the whole antibody, a dimer, an individual light and/or heavy chain, or other immunoglobulin form, may be purified according to available purification procedures, including for example, by chromatography (e.g., ion exchange, affinity, particularly by affinity for the specific antigen after Protein A, and sizing column chromatography), centrifugation, differential solubility, e.g. ammonium sulfate precipitation, or by any other standard technique for the purification of proteins; see, e.g., Scopes, "Protein Purification", Springer Verlag, N.Y. (1982).

Detection of N-Glycanase 1 (NGLY-1) and Diagnosis of NGLY-1 Deficiency

Another aspect of the present disclosure provides methods of detecting N-glycanase 1 (NGLY-1) and diagnosing NGLY-1 deficiency using an antibody described herein. These methods may also be used to monitor the efficacy of a NGLY-1 deficiency therapy. As the anti-NGLY-1 antibodies described herein have strong binding affinity for NGLY-1 and are useful for detecting the presence of NGLY-1 in a biological sample, a lack of anti-NGLY-1 antibody binding, or binding of the anti-NGLY-1 antibody below a particular threshold relative to a control, is indicative of NGLY-1 deficiency. The term "detecting", as used herein, refers to quantitative and/or qualitative detection.

In some embodiments, an anti-NGLY-1 antibody for use in a method of diagnosis or detection is provided. For example, a method of detecting the presence (or absence) of NGLY-1 in a biological sample is provided. In some embodiments, a method comprises contacting the biological sample with an anti-NGLY-1 antibody as described herein under conditions permissive for binding of the anti-NGLY-1 antibody to NGLY-1, and detecting whether a complex is formed between the anti-NGLY-1 antibody and NGLY-1. Such method may be performed in vitro, for example. The presence of the anti-NGLY-1 antibody-NGLY-1 complex may be indicative of a healthy subject (at a subject who does not have a NGLY-1 deficiency), whereas a lack of complex formation may indicate that the subject has a NGLY-1 deficiency.

Likewise, the level of NGLY-1 may be monitored over time, for example, to determine the efficacy of an NGLY-1 deficiency therapy. Monitoring may take place at evenly-spaced intervals, for example daily, every 2 days, every 3 days, every 4 days, every 5 days, every 6 days, weekly, biweekly, every third week, monthly, bimonthly, every 3rd month, every 4th month, every 5th month, every 6th month, every 7th month, every 8th month, every 9 month, every 10th month, every 11th month, or annually. In some embodiments, the monitoring occurs at differently-spaced intervals. For example, if a subject's NGLY-1 levels increase over a monitoring period, less frequent monitoring may be required. Conversely, if a subject's NGLY-1 levels decrease over a monitoring period, more frequent monitoring may be required. In some embodiments, the level of NGLY-1 present in a subject's sample may be compared to that of a reference sample. A "reference sample," as used herein, refers to a sample from an individual who does not have an NGLY-1 deficiency or a sample from an individual who does have an NGLY-1 deficiency. As an example, efficacious treatment may be indicated when a subject undergoing an NGLY-1 deficiency treatment having an NGLY-1 level greater than that of the reference sample from a subject who has an NGLY-1 deficiency may be indicative of efficacious treatment.

Detection of the anti-NGLY-1 antibody binding may be performed using any method available in the art, including immunoassays, including, for example, immunohistochemistry (IHC), immunofluorescence (IF), immunoblotting (e.g., Western blotting), flow cytometry (e.g., FACS™), and Enzyme-linked Immunosorbant Assay (ELISA). In some embodiments, immunoblotting is used for detection.

Therefore, in some embodiments, the antibody is conjugated to a detectable label (antibody-label conjugate), such as an enzyme, radioisotope, fluorophore, heavy metal (colloidal metals), or luminescent molecule. Examples of detectable labels include, but are not limited to, luciferase, green fluorescent protein (GFP), chloramphenicol acetyl transferase (CAT), $^{32}$P, $^{33}$P, $^{14}$C, $^{125}$I, $^{131}$I, $^{35}$S, $^{3}$H, fluorescein, fluorescein isothiocyanate (FITC), DyLight 488, phycoerythrin (PE), propidium iodide (PI), PerCP, PE-Alexa Fluor® 700, Cy5, allophycocyanin, Cy7, any of a variety of luminescent lanthanide (e.g., europium or terbium) chelates (e.g., the europium chelate of diethylene triamine pentaacetic acid (DTPA) or tetraazacyclododecane-1,4, 7,10-tetraacetic acid (DOTA)), alkaline phosphatase, horseradish peroxidase, gold, copper, mercury, and cadmium. The detectable label(s) may be incorporated into the anti-NGLY-1 antibody as fusion proteins, in some embodiments. Methods for generating nucleic acids encoding an antibody-heterologous polypeptide fusion protein are well known in the art of antibody engineering and described in, e.g., Dakappagari et al. (2006) J Immunol 176:426-440.

The disclosure further provides for the use of an anti-NGLY-1 antibody in a method of diagnosing a subject suffering from a disorder (e.g., NGLY-1 deficiency), the method comprising: determining the presence or expression level of NGLY-1 in a sample obtained from the subject by contacting the sample with an anti-NGLY-1 antibody described herein and detecting the presence of the bound antibody. The biological sample refers to a subset of tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen) from a subject. A sample further can include a homogenate, lysate or extract prepared from a subject or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs.

The disclosure yet further provides for the use of an anti-NGLY-1 antibody in the manufacture of a reagent for use in a method of diagnosing a subject suffering from a disorder (e.g., NGLY-1 deficiency), the method comprising: determining the presence or expression level of NGLY-1 in a sample obtained from the subject by contacting the sample with an anti-NGLY-1 antibody of the disclosure and detecting the presence of the bound antibody.

Provided herein are kits which include the diagnostic anti-NGLY-1 antibodies described herein and instructions for use. Accordingly, in some embodiments, the kit comprises an antibody comprising the heavy and light chain variable region CDR sequences set forth in SEQ ID NOs: 3-5 and 14-16, respectively, heavy and light chain variable region sequences set forth in SEQ ID NOs: 10 and 21, respectively, wherein the antibody or antigen-binding fragment thereof specifically binds to human NGLY-1, or full length heavy and light chain sequences set forth in SEQ ID NOs: 1 and 2, respectively. In certain embodiments, the antibody comprises a detectable label, e.g., an antibody-label conjugate. Such kits may comprise at least one additional reagent. For example, in some embodiments, the kits comprise buffers, stabilizers, substrates, at least one immunodetection reagent (e.g., secondary antibodies for use in immunohistochemistry), and/or cofactors required for the assay. In some embodiments, the antibody and, optionally the reagents, are suitably aliquoted. In some embodiments, the kit comprises a means for obtaining the biological sample from a subject. Such means can comprise, for example, reagents that can be used to obtain fluid or tissue sample from the subject.

Pharmaceutical Compositions The disclosure, in some aspects, provides pharmaceutical compositions comprising an antibody described herein and a pharmaceutically-acceptable carrier. A "pharmaceutically acceptable carrier," after administration to or upon a subject (e.g., a human), does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

In some embodiments, the composition further comprises an additional agent for treating an NGLY-1 deficiency, for example, enzyme replacement therapy, and/or proton pump inhibitors (ENGase inhibitors) (Bi et al., Bioorg Med Chem Lett. 2017; 27:2962-6).

In some embodiments, the composition is a diagnostic composition and further comprises at least one reagent for use the immune- and/or nucleic acid-based diagnostic methods described herein. For example, the reagents includes, but are not limited to, those used in immunoassays, including, for example, immunohistochemistry (IHC), immunofluorescence (IF), immunoblotting (e.g., Western blotting), flow cytometry (e.g., FACS™), and Enzyme-linked Immunosorbant Assay (ELISA). Such reagents are specific to the type of diagnostic method used, and are known in the art.

Methods of Treatment

In some embodiments, the present disclosure provides methods of treating a disease or disorder in a patient comprising administering to the patient in need thereof a therapeutically effective amount of an antibody that binds NGLY-1 protein. In some embodiments, the disease or disorder is cancer. The cancer may be a carcinoma, sarcoma, lymphoma, leukemia, melanoma, mesothelioma, multiple myeloma, or seminoma or the cancer may be melanoma, ovarian cancer, breast cancer, cervical cancer, endometrial cancer, colon cancer, pancreatic cancer, prostate cancer, liver cancer, renal cancer, lung cancer, glioma, or lymphoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the cancer is glioma, liver cancer, or melanoma. The cancer, in some embodiments, is a melanoma.

In some embodiments, the methods further comprise administering a second agent/cancer therapy such as surgery, a second chemotherapeutic agent, a radiotherapy, or an immunotherapy. The second chemotherapeutic agent, in some embodiments, is an alkylating agent or an alkylating-like agent such as cisplatin, dacarbazine, or temozolomide.

In some embodiments, a pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularly, intravitreally, liposomally, locally, mucosally, parenterally, rectally, subconjunctivally, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. In some embodiments, a pharmaceutical composition is formulated as a unit dose.

A pharmaceutical composition may be administered to a mammal (e.g., rodent, human, non-human primates, canine, bovine, ovine, equine, feline, etc.) in an effective amount, that is, an amount capable of producing a desirable result in a treated subject (e.g., causing apoptosis of cancerous cells). Toxicity and therapeutic efficacy of the compositions utilized in methods of the disclosure can be determined by available pharmaceutical procedures. Dosage for any one subject depends on many factors, including the subject's size, body surface area, body weight, age, the particular composition to be administered, time and route of administration, general health, the clinical symptoms of the infection or cancer and other drugs being administered concurrently. A composition as described herein is typically administered at a dosage that induces death of cancerous cells (e.g., induces apoptosis of a cancer cell), as assayed by identifying a reduction in hematological parameters (complete blood count—CBC), or cancer cell growth or proliferation.

EXAMPLES

Example 1

Figure 1:
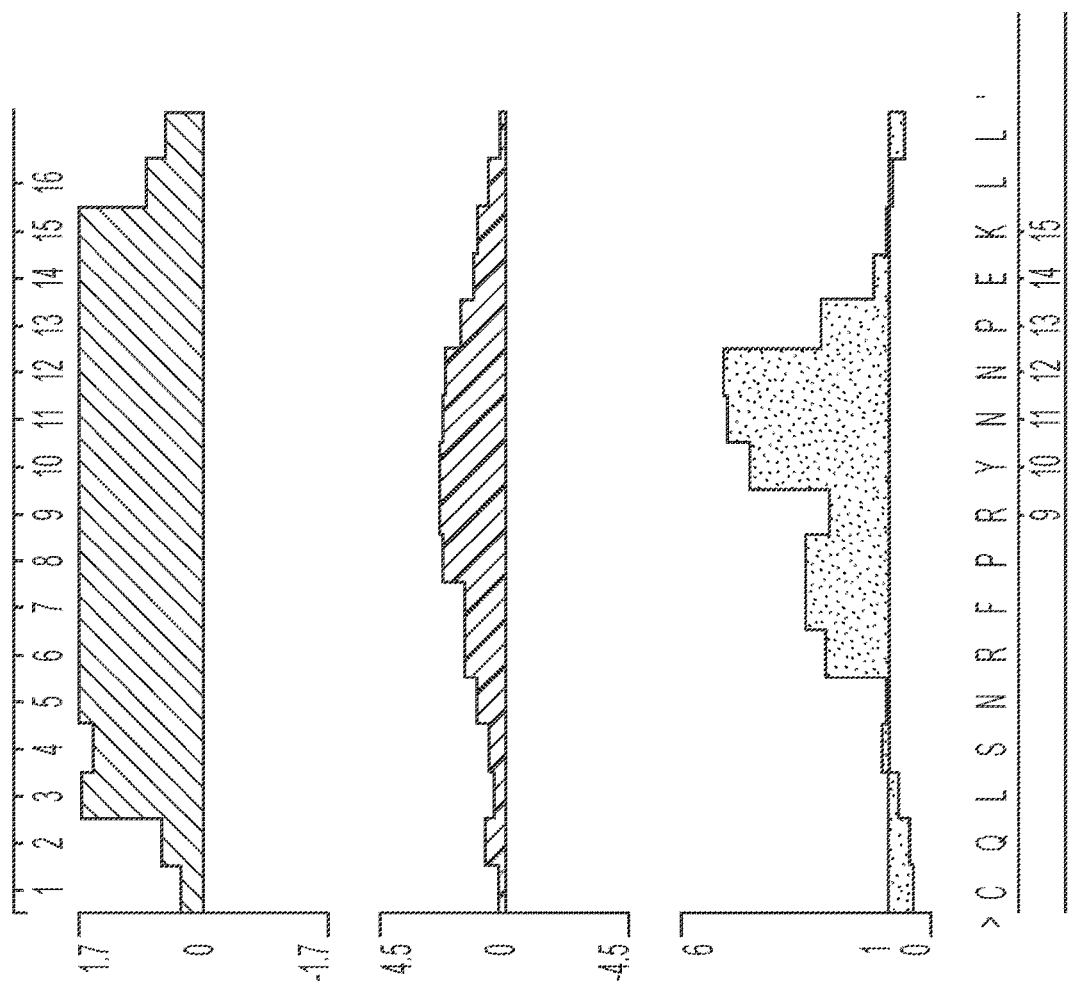
FIG. 1 shows an antigen index plot (top), a hydrophilicity plot (middle), and a surface probability plot (bottom) of NGly-1 amino acid sequences 283 to 299 (SEQ ID NO: 45).
Figure 2:
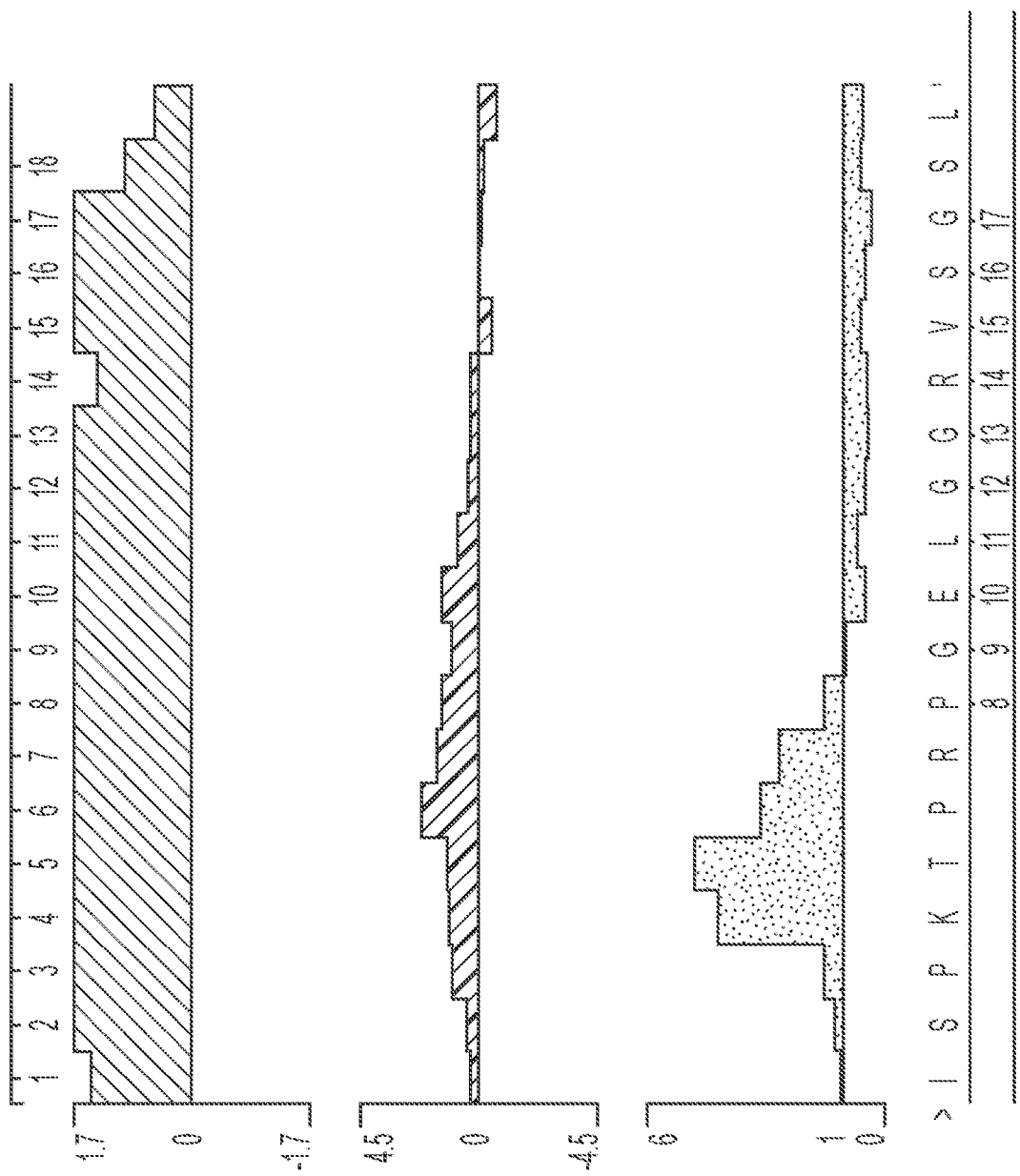
FIG. 2 shows an antigen index plot (top), a hydrophilicity plot (middle), and a surface probability plot (bottom) of NGly-1 amino acid sequences 442 to 460 (SEQ ID NO: 46).

The protein sequence of Mouse Ngly1 was obtained from the STRING interaction networks database (string-db.org). The sequence was loaded into the DNASTAR software package using the EditSeq application. The EditSeq file was then loaded into the Protean application to generate a plot of specific physico-chemical properties:

1) Antigenic Index using the Jameson Wolf algorithm
2) Hydrophilicity using the Kyle Doolittle algorithm
3) Surface probability plot using the Emini algorithm Two peptide candidates were selected for review in 3-D models based on high antigenic index, high hydrophilicity and high surface probability representing amino acid stretches 283-299 (FIG. 1) and 442-460 (FIG. 2).

3-D models were generated using the Max Planck Institute's MPI Bioinformatics Toolkit, specifically the HHpred modeling tool. Atomic coordinates from this were loaded into a local copy of MacPyMol 3-D modeling and rendering software and a 3-D model generated.

Figure 3:
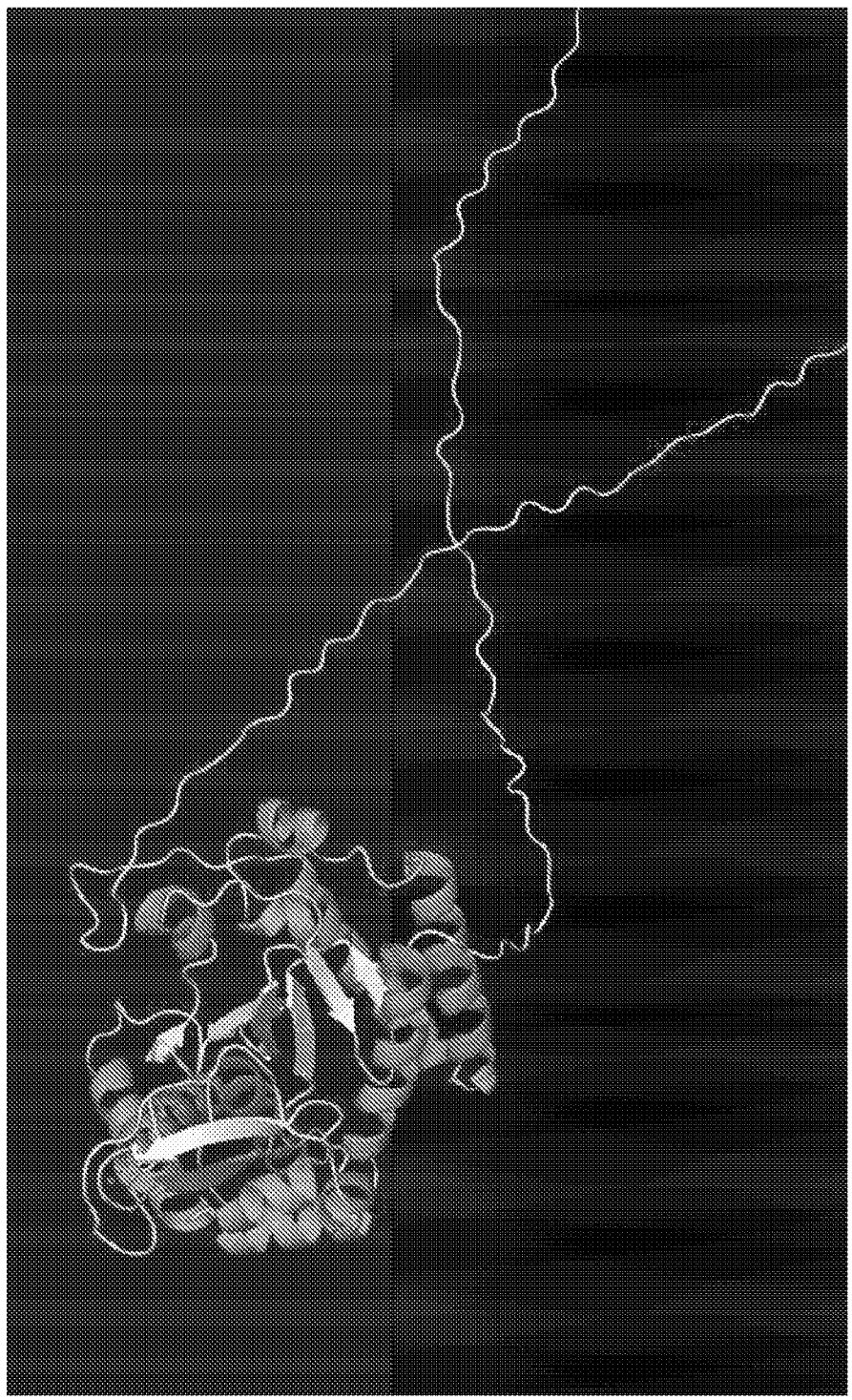
FIG. 3 shows the structure of full length NGLyc-1 with two candidate peptides selected.
Figure 4:
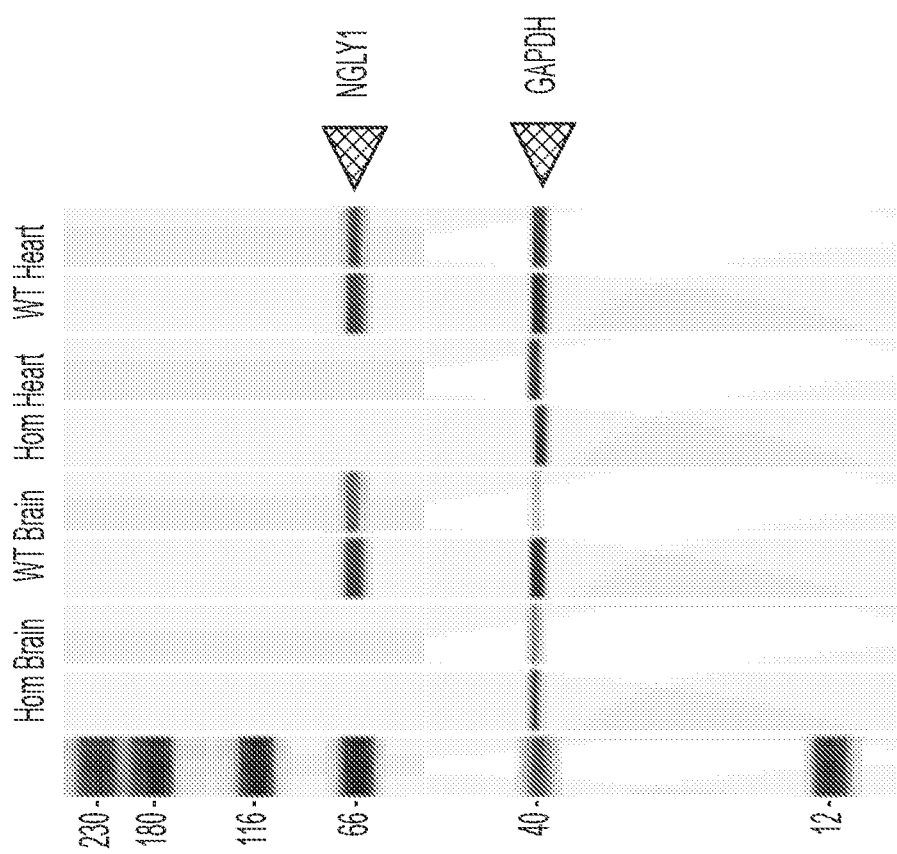
FIG. 4 shows data demonstrating anti-NGly-1 specificity of the monoclonal antibody of the present disclosure. Tissues were collected from embryonic E16.5 day brain and heart using C57BL/6J (WT) and JR 27060 Ngly-1 null homozygous tissues (HOM).
Figure 5:
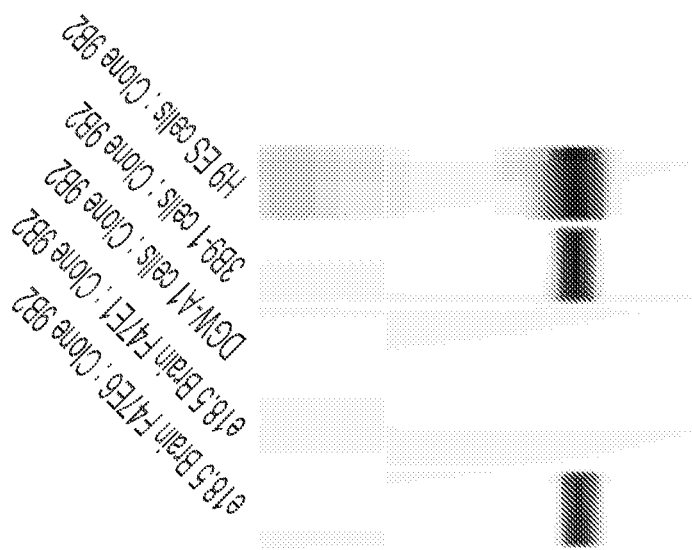
FIG. 5 shows data demonstrating that the mouse anti-NGly-1 monoclonal antibody of the present disclosure cross-reacts with human NGLY-1. Lane 1: F47E6 Mouse C57BL/6J (WT); Lane 2: F47E1 27060 Mouse Ngly-1 null mutant; Lane 3: Human iPSC cell: DGW-A1 (NGLY 1 double mutant)—derived from an affected patient; Lane 4: Human iPSC cell: 39B9-1 (one allele of the double mutant of NGLY-1 corrected); Lane 5: Human H9 Wild-type ES cells.
Figure 6:
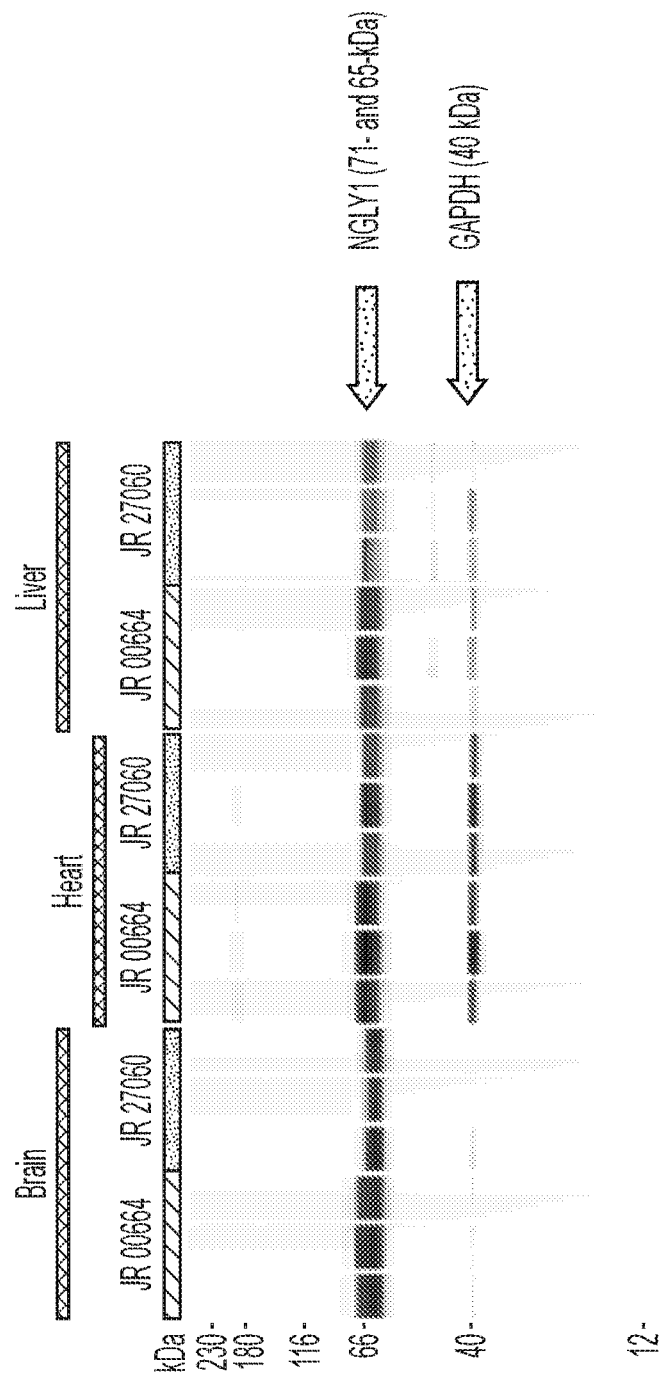
FIG. 6 shows data demonstrating that one of the publicly-available anti-NGly-1 antibodies detects a cross reactive protein that is very similar in size to the native mouse NGly-1 protein, indicating that the antibody is not specific for NGly-1. The tissues used were isolated from B57BL/6J (JR 00664) and homozygous Ngly1 null (JR 27060) embryos, aged E16.5 days.
Figure 7:
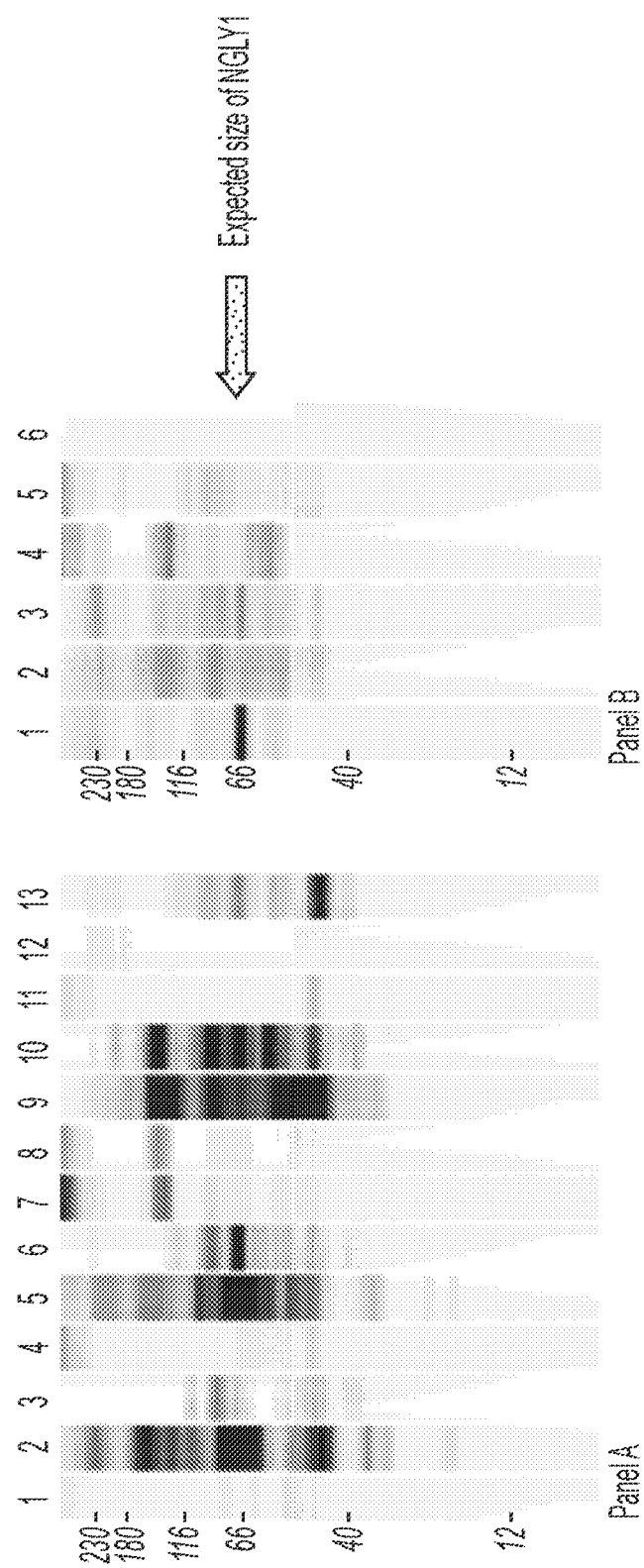
FIG. 7 shows data demonstrating that a commercially-available anti-NGly-1 antibody (SIGMA) is not specific for NGly-1. Predominant bands of the expected size are seen in Lanes 2, 6, 9, 10, 13 of Panel A and Lane 1 of Panel B. Panel A—Lane 1: JR00664 Heart Total Extract; Lane 2: JR 00664 Heart Mitochondrial Fraction; Lane 3: JR 00664 Heart Cytosolic Fraction; Lane 4: JR00664 Kidney Total extract; Lane 5: JR 00664 Kidney Mitochondrial Fraction; Lane 6: JR 00664 Kidney Cytosolic Fraction; Lane 7: JR00664 Liver Total Extract; Lane 8: JR27962 Liver Mitochondrial Fraction; Lane 9: JR 00664 Liver Mitochondrial Fraction; Lane 10: JR00664 Liver Cytosolic Fraction; Lane 11: JR 00664 Skeletal Muscle Mitochondrial Fraction; Lane 12: JR 00664 Skeletal Muscle Mitochondrial Fraction; Lane 13: JR 00664 Skeletal Muscle Cytosolic Fraction. Panel B—Lane 1: C2C12 Mouse myocyte cell line; Lane 2: 2H11 Mouse endothelial cell line; Lane 3: mK4 Human embryonic kidney cell line; Lane 4: NIH 3T3 Mouse fibroblast cell line; Lane 5: JR 00664 Brain total extract; Lane 6: No lysate control. Tissue was obtained from a JR00664 C57BL/6J mouse strain and JR27962 C57BL/6J-Ngly lem9Lutzy/J (an Ngly1 deficient) mouse strain.
Figure 8A:
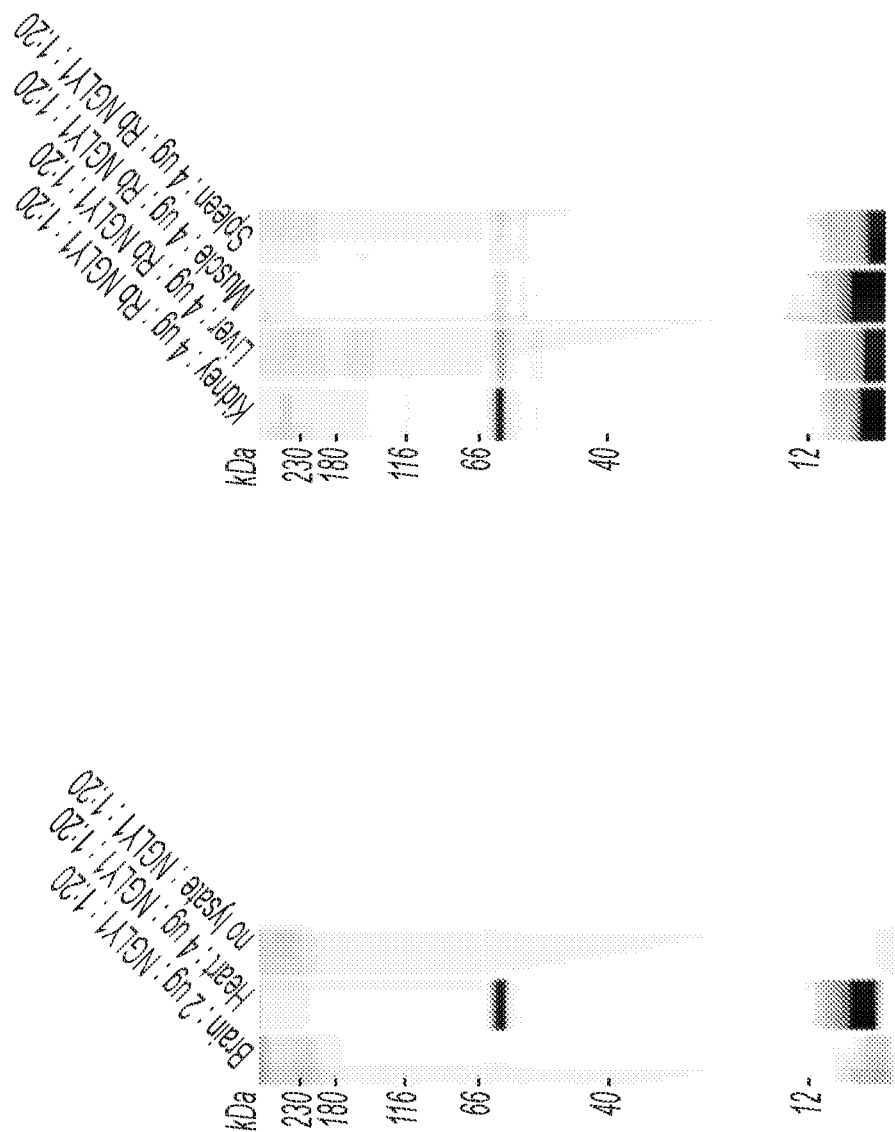
FIGS. 8A and 8B show data demonstrating detection of a 62 kDa polypeptide in mouse C57BL/6J tissues using another commercially-available anti-NGly-1 antibody (AB-CAM). This is a smaller protein than observed using the anti-NGly-1 monoclonal antibody of the present disclosure. Further, a strong cross-reactivity was detected against a small 2-3 kDa polypeptide using the commercially-available anti-NGly-1 antibody, and no expression of the 62 kDa protein was detected in brain tissue. This suggests that the protein(s) detected with this commercially-available antibody may not be mouse NGly-1.
Figure 8B:
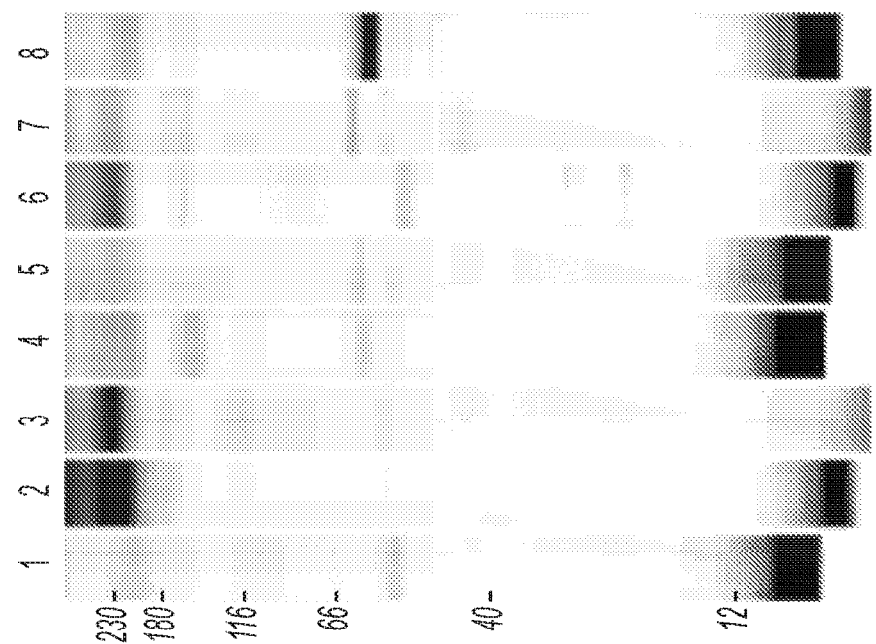

Peptide 1, a 17-mer amino acid peptide CQLSNRF-PRYNNPEKLL (SEQ ID NO: 45) derived from murine Ngly1 amino acids 283-299, inclusive, was selected and highlighted in magenta; and Peptide 2 (SEQ ID NO: 46) representing amino acids 442 to 460 was selected and highlighted in cyan (FIG. 3).

Peptide 2 was rejected as a peptide candidate due to it being structured and relatively inaccessible. Peptide 1 showed a disordered region with high accessibility and synthesis of this peptide was ordered through Peptide Specialty Labs GmbH in Heidelberg, Germany. The peptide sequence is identical to the syntenic region in human NGLY1, except for a single polymorphism in the third amino acid. The amino acid is leucine in the mouse and phenylalanine in human. A portion of the peptide was conjugated to the diphtheria-toxoid carrier protein for immunization.

The conjugate was injected into female BALB/cJ mice at a dose of 10 ug per mouse with Alum adjuvant. Mice were immunized by i.p injection three times approximately two (2) weeks apart. Ten days after the third immunization, splenocytes were isolated and fused with SP2 myeloma cells to create hybridoma cell lines. Hybridomas were cultured in 96-well plates and supernatants screened on protein arrays and by ELISA. Positive clones were further validated by western blot using lysates prepared from C57BL/6J and the CRISPR/Cas9 generated null strain as positive and negative controls. Additional immunoblots were used to identify additional clones that generated antibodies capable of cross reacting with human NGLY1 protein. Isogenic human derived NGLY1 null and wild type iPS cell lines providing positive and negative controls evaluation of anti-human NGLY1 cross-reactivity were provided. A single hybridoma gave rise to clone 5G8 that generated an antibody that was specific to both murine and human NGLY1 protein and was used for subsequent studies.

TABLE 1

Anti-NGly-1 Antibody Amino Acid Sequences

| Antibody Component | Amino Acid Sequence | SEQ ID NO: |
|---|---|---|
| Heavy Chain | QVQLQQSGAELVRPGTSVKVSCKASGYAFINYLIEWVKQRPGQGLEWIG IISPGSGSTNYNEEFRGRATLTADRSSSTAYMQLSSLTSDDSAVYFCARG GLTHYSGSTYEEGFDFWGQGTTLTVSSAKTTPPSVYPLAPGSAAQTNSM VTLGCLVKGYFPEPVTVTWNSGSLSSGVHTFPAVLQSDLYTLSSSVTVPS STWPSETVTCNVAHPASSTKVDKKIVPRDCGCKPCICTVPEVSSVFIFPPK PKDVLTITLTPKVTCVVVDISKDDPEVQFSWFVDDVEVHTAQTQPREEQF NSTFRSVSELPIMHQDWLNGKEFKCRVNSAAFPAPIEKTISKTKGRPKAP QVYTIPPPKEQMAKDKVSLTCMITDFFPEDITVEWQWNGQPAENYKNTQ PIMDTDGSYFVYSKLNVQKSNWEAGNTFTCSVLHEGLHNHHTEKSLSHS PGK | 1 |
| Heavy Chain with leader sequence | MEWSGVFIFLLSVTAGIHSQVQLQQSGAELVRPGTSVKVSCKASGYAFIN YLIEWVKQRPGQGLEWIGIISPGSGSTNYNEEFRGRATLTADRSSSTAYM QLSSLTSDDSAVYFCARGGLTHYSGSTYEEGFDFWGQGTTLTVSSAKTTP PSVYPLAPGSAAQTNSMVTLGCLVKGYFPEPVTVTWNSGSLSSGVHTFP AVLQSDLYTLSSSVTVPSSTWPSETVTCNVAHPASSTKVDKKIVPRDCGC KPCICTVPEVSSVFIFPPKPKDVLTITLTPKVTCVVVDISKDDPEVQFSWFV DDVEVHTAQTQPREEQFNSTFRSVSELPIMHQDWLNGKEFKCRVNSAAF PAPIEKTISKTKGRPKAPQVYTIPPPKEQMAKDKVSLTCMITDFFPEDITVE WQWNGQPAENYKNTQPIMDTDGSYFVYSKLNVQKSNWEAGNTFTCSV LHEGLHNHHTEKSLSHSPGK | 2 |
| VH CDR1 | NYLIE | 3 |
| VH CDR2 | IISPGSGSTNYNEEFRG | 4 |
| VH CDR3 | GGLTHYSGSTYEEGFDF | 5 |
| VH FR1 | QVQLQQSGAELVRPGTSVKVSCKASGYAFI | 6 |
| VH FR2 | WVKQRPGQGLEWIG | 7 |
| VH FR3 | RATLTADRSSSTAYMQLSSLTSDDSAVYFCAR | 8 |
| VH FR4 | WGQGTTLTVSS | 9 |
| HC Variable | QVQLQQSGAELVRPGTSVKVSCKASGYAFINYLIEWVKQRPGQGLEWIG IISPGSGSTNYNEEFRGRATLTADRSSSTAYMQLSSLTSDDSAVYFCARG GLTHYSGSTYEEGFDFWGQGTTLTVSS | 10 |
| HC Constant | AKTTPPSVYPLAPGSAAQTNSMVTLGCLVKGYFPEPVTVTWNSGSLSSG VHTFPAVLQSDLYTLSSSVTVPSSTWPSETVTCNVAHPASSTKVDKKIVP RDCGCKPCICTVPEVSSVFIFPPKPKDVLTITLTPKVTCVVVDISKDDPEV QFSWFVDDVEVHTAQTQPREEQFNSTFRSVSELPIMHQDWLNGKEFKCR VNSAAFPAPIEKTISKTKGRPKAPQVYTIPPPKEQMAKDKVSLTCMITDFF PEDITVEWQWNGQPAENYKNTQPIMDTDGSYFVYSKLNVQKSNWEAGN TFTCSVLHEGLHNHHTEKSLSHSPGK | 11 |

TABLE 1-continued

Anti-NGly-1 Antibody Amino Acid Sequences

| Antibody Component | Amino Acid Sequence | SEQ ID NO: |
|---|---|---|
| Light Chain | QAVVTQESALTTSPGETVTLTCRSSTGAVTTTNYANWVQEKPDHLFTGLI GGTNNRAPGVPARFSGSLIGDKAALTITGAQTDDEAIYFCALWYSNRWV FGGGTKLTVLGQPKSSPSVTLFPPSSEELETNKATLVCTITDFYPGVVTVD WKVDGTPVTQGMETTQPSKQSNNKYMASSYLTLTARAWERHSSYSCQV THEGHTVEKSLSRADCS | 12 |
| Light Chain with leader sequence | MAWISLILSLLALSSGAISQAVVTQESALTTSPGETVTLTCRSSTGAVTTT NYANWVQEKPDHLFTGLIGGTNNRAPGVPARFSGSLIGDKAALTITGAQ TDDEAIYFCALWYSNRWVFGGGTKLTVLGQPKSSPSVTLFPPSSEELETN KATLVCTITDFYPGVVTVDWKVDGTPVTQGMETTQPSKQSNNKYMASS YLTLTARAWERHSSYSCQVTHEGHTVEKSLSRADCS | 13 |
| VL CDR1 | RSSTGAVTTTNYAN | 14 |
| VL CDR2 | GTNNRAP | 15 |
| VL CDR3 | ALWYSNRWV | 16 |
| VL FR1 | QAVVTQESALTTSPGETVTLTC | 17 |
| VL FR2 | WVQEKPDHLFTGLIG | 18 |
| VL FR3 | GVPARFSGSLIGDKAALTITGAQTDDEAIYFC | 19 |
| VL FR4 | FGGGTKLTVL | 20 |
| LC Variable | QAVVTQESALTTSPGETVTLTCRSSTGAVTTTNYANWVQEKPDHLFTGLI GGTNNRAPGVPARFSGSLIGDKAALTITGAQTDDEAIYFCALWYSNRWV FGGGTKLTVL | 21 |
| LC Constant | GQPKSSPSVTLFPPSSEELETNKATLVCTITDFYPGVVTVDWKVDGTPVT QGMETTQPSKQSNNKYMASSYLTLTARAWERHSSYSCQVTHEGHTVEK SLSRADCS | 22 |

*This sequence may include a stop sequence, such as TGA
Leader sequence is underlined.

TABLE 2

Anti-NGly-1 Antibody Nucleic Acid Sequences

| Antibody Component | Nucleic Acid Sequence | SEQ ID NO: |
|---|---|---|
| Heavy Chain | CAGGTCCAACTGCAGCAGTCTGGAGCTGAACTGGTAAGGCCGGGGAC TTCAGTGAAGGTGTCCTGCAAGGCTTCTGGATACGCCTTCATTAATTA CTTGATAGAATGGGTGAAACAGAGGCCTGGACAGGGCCTTGAGTGGA TTGGAATAATAAGTCCTGGAAGTGGTAGTACTAACTACAATGAAGAG TTCAGGGGCAGGGCAACACTGACTGCAGACAGATCCTCCAGCACTGC CTACATGCAGCTCAGCAGCCTGACATCTGATGACTCTGCGGTCTATTT CTGTGCAAGAGGGGGCTTAACTCATTACTCCGGCAGTACGTACGAAG AGGGCTTTGACTTCTGGGGCCAAGGCACCACTCTCACAGTCTCCTCAG CCAAAACGACACCCCCATCTGTCTATCCACTGGCCCCTGGATCTGCTG CCCAAACTAACTCCATGGTGACCCTGGGATGCCTGGTCAAGGGCTATT TCCCTGAGCCAGTGACAGTGACCTGGAACTCTGGATCCCTGTCCAGCG GTGTGCACACCTTCCCAGCTGTCCTGCAGTCTGACCTCTACACTCTGA GCAGCTCAGTGACTGTCCCCTCCAGCACCTGGCCCAGCGAGACCGTC ACCTGCAACGTTGCCCACCCGGCCAGCAGCACCAAGGTGGACAAGAA AATTGTGCCCAGGGATTGTGGTTGTAAGCCTTGCATATGTACAGTCCC AGAAGTATCATCTGTCTTCATCTTCCCCCCAAAGCCCAAGGATGTGCT CACCATTACTCTGACTCCTAAGGTCACGTGTGTTGTGGTAGACATCAG CAAGGATGATCCCGAGGTCCAGTTCAGCTGGTTTGTAGATGATGTGG AGGTGCACACAGCTCAGACGCAACCCCGGGAGGAGCAGTTCAACAGC ACTTTCCGCTCAGTCAGTGAACTTCCCATCATGCACCAGGACTGGCTC AATGGCAAGGAGTTCAAATGCAGGGTCAACAGTGCAGCTTTCCCTGC CCCCATCGAGAAAACCATCTCCAAAACCAAAGGCAGACCGAAGGCTC CACAGGTGTACACCATTCCACCTCCCAAGGAGCAGATGGCCAAGGAT AAAGTCAGTCTGACCTGCATGATAACAGACTTCTTCCCTGAAGACATT ACTGTGGAGTGGCAGTGGAATGGGCAGCCAGCGGAGAACTACAAGA ACACTCAGCCCATCATGGACACAGATGGCTCTTACTTCGTCTACAGCA AGCTCAATGTGCAGAAGAGCAACTGGGAGGCAGGAAATACTTTCACC TGCTCTGTGTTACATGAGGGCCTGCACAACCACCATACTGAGAAGAG CCTCTCCCACTCTCCTGGTAAA* | 23 |

TABLE 2-continued

Anti-NGly-1 Antibody Nucleic Acid Sequences

| Antibody Component | Nucleic Acid Sequence | SEQ ID NO: |
|---|---|---|
| Heavy Chain with leader sequence | ATGGAATGGAGCGGAGTCTTTATCTTTCTCCTGTCAGTAACTGCAGGT<br>ATTCACTCCCAGGTCCAACTGCAGCAGTCTGGAGCTGAACTGGTAAG<br>GCCGGGGACTTCAGTGAAGGTGTCCTGCAAGGCTTCTGGATACGCCTT<br>CATTAATTACTTGATAGAATGGGTGAAACAGAGGCCTGGACAGGGCC<br>TTGAGTGGATTGGAATAATAAGTCCTGGAAGTGGTAGTACTAACTAC<br>AATGAAGAGTTCAGGGGCAGGGCAACACTGACTGCAGACAGATCCTC<br>CAGCACTGCCTACATGCAGCTCAGCAGCCTGACATCTGATGACTCTGC<br>GGTCTATTTCTGTGCAAGAGGGGGCTTAACTCATTACTCCGGCAGTAC<br>GTACGAAGAGGGCTTTGACTTCTGGGGCCAAGGCACCACTCTCACAG<br>TCTCCTCAGCCAAAACGACACCCCCATCTGTCTATCCACTGGCCCCTG<br>GATCTGCTGCCCAAACTAACTCCATGGTGACCCTGGGATGCCTGGTCA<br>AGGGCTATTTCCCTGAGCCAGTGACAGTGACCTGGAACTCTGGATCCC<br>TGTCCAGCGGTGTGCACACCTTCCCAGCTGTCCTGCAGTCTGACCTCT<br>ACACTCTGAGCAGCTCAGTGACTGTCCCCTCCAGCACCTGGCCCAGCG<br>AGACCGTCACCTGCAACGTTGCCCACCCGGCCAGCAGCACCAAGGTG<br>GACAAGAAATTGTGCCCAGGGATTGTGGTTGTAAGCCTTGCATATG<br>TACAGTCCCAGAAGTATCATCTGTCTTCATCTTCCCCCAAAGCCCAA<br>GGATGTGCTCACCATTACTCTGACTCCTAAGGTCACGTGTGTTGTGGT<br>AGACATCAGCAAGGATGATCCCGAGGTCCAGTTCAGCTGGTTTGTAG<br>ATGATGTGGAGGTGCACACAGCTCAGACGCAACCCCGGGAGGAGCA<br>GTTCAACAGCACTTTCCGCTCAGTCAGTGAACTTCCCATCATGCACCA<br>GGACTGGCTCAATGGCAAGGAGTTCAAATGCAGGGTCAACAGTGCAG<br>CTTTCCCTGCCCCCATCGAGAAAACCATCTCCAAAACCAAAGGCAGA<br>CCGAAGGCTCCACAGGTGTACACCATTCCACCTCCCAAGGAGCAGAT<br>GGCCAAGGATAAAGTCAGTCTGACCTGCATGATAACAGACTTCTTCC<br>CTGAAGACATTACTGTGGAGTGGCAGTGGAATGGGCAGCCAGCGGAG<br>AACTACAAGAACACTCAGCCCATCATGGACACAGATGGCTCTTACTT<br>CGTCTACAGCAAGCTCAATGTGCAGAAGAGCAACTGGGAGGCAGGA<br>AATACTTTCACCTGCTCTGTGTTACATGAGGGCCTGCACAACCACCAT<br>ACTGAGAAGAGCCTCTCCCACTCTCCTGGTAAA* | 24 |
| VH CDR1 | AATTACTTGATAGAA | 25 |
| VH CDR2 | ATAATAAGTCCTGGAAGTGGTAGTACTAACTACAATGAAGAGTTCAG<br>GGGC | 26 |
| VH CDR3 | GGGGGCTTAACTCATTACTCCGGCAGTACGTACGAAGAGGGCTTTGA<br>CTTC | 27 |
| VH FR1 | CAGGTCCAACTGCAGCAGTCTGGAGCTGAACTGGTAAGGCCGGGGAC<br>TTCAGTGAAGGTGTCCTGCAAGGCTTCTGGATACGCCTTCATT | 28 |
| VH FR2 | TGGGTGAAACAGAGGCCTGGACAGGGCCTTGAGTGGATTGGA | 29 |
| VH FR3 | AGGGCAACACTGACTGCAGACAGATCCTCCAGCACTGCCTACATGCA<br>GCTCAGCAGCCTGACATCTGATGACTCTGCGGTCTATTTCTGTGCAAG<br>A | 30 |
| VH FR4 | TGGGGCCAAGGCACCACTCTCACAGTCTCCTCA | 31 |
| HC Variable | CAGGTCCAACTGCAGCAGTCTGGAGCTGAACTGGTAAGGCCGGGGAC<br>TTCAGTGAAGGTGTCCTGCAAGGCTTCTGGATACGCCTTCATTAATTA<br>CTTGATAGAATGGGTGAAACAGAGGCCTGGACAGGGCCTTGAGTGGA<br>TTGGAATAATAAGTCCTGGAAGTGGTAGTACTAACTACAATGAAGAG<br>TTCAGGGGCAGGGCAACACTGACTGCAGACAGATCCTCCAGCACTGC<br>CTACATGCAGCTCAGCAGCCTGACATCTGATGACTCTGCGGTCTATTT<br>CTGTGCAAGAGGGGGCTTAACTCATTACTCCGGCAGTACGTACGAAG<br>AGGGCTTTGACTTCTGGGGCCAAGGCACCACTCTCACAGTCTCCTCA | 32 |
| HC Constant | GCCAAAACGACACCCCCATCTGTCTATCCACTGGCCCCTGGATCTGCT<br>GCCCAAACTAACTCCATGGTGACCCTGGGATGCCTGGTCAAGGGCTA<br>TTTCCCTGAGCCAGTGACAGTGACCTGGAACTCTGGATCCCTGTCCAG<br>CGGTGTGCACACCTTCCCAGCTGTCCTGCAGTCTGACCTCTACACTCT<br>GAGCAGCTCAGTGACTGTCCCCTCCAGCACCTGGCCCAGCGAGACCG<br>TCACCTGCAACGTTGCCCACCCGGCCAGCAGCACCAAGGTGGACAAG<br>AAAATTGTGCCCAGGGATTGTGGTTGTAAGCCTTGCATATGTACAGTC<br>CCAGAAGTATCATCTGTCTTCATCTTCCCCCAAAGCCCAAGGATGTG<br>CTCACCATTACTCTGACTCCTAAGGTCACGTGTGTTGTGGTAGACATC<br>AGCAAGGATGATCCCGAGGTCCAGTTCAGCTGGTTTGTAGATGATGT<br>GGAGGTGCACACAGCTCAGACGCAACCCCGGGAGGAGCAGTTCAAC<br>AGCACTTTCCGCTCAGTCAGTGAACTTCCCATCATGCACCAGGACTGG<br>CTCAATGGCAAGGAGTTCAAATGCAGGGTCAACAGTGCAGCTTTCCC<br>TGCCCCCATCGAGAAAACCATCTCCAAAACCAAAGGCAGACCGAAGG<br>CTCCACAGGTGTACACCATTCCACCTCCCAAGGAGCAGATGGCCAAG | 33 |

TABLE 2-continued

Anti-NGly-1 Antibody Nucleic Acid Sequences

| Antibody Component | Nucleic Acid Sequence | SEQ ID NO: |
|---|---|---|
| | GATAAAGTCAGTCTGACCTGCATGATAACAGACTTCTTCCCTGAAGAC ATTACTGTGGAGTGGCAGTGGAATGGGCAGCCAGCGGAGAACTACAA GAACACTCAGCCCATCATGGACACAGATGGCTCTTACTTCGTCTACAG CAAGCTCAATGTGCAGAAGAGCAACTGGGAGGCAGGAAATACTTTCA CCTGCTCTGTGTTACATGAGGGCCTGCACAACCACCATACTGAGAAG AGCCTCTCCCACTCTCCTGGTAAA* | |
| Light Chain | CAGGCTGTTGTGACTCAGGAATCTGCACTCACCACATCACCTGGTGAA ACAGTCACACTCACTTGTCGCTCAAGTACTGGGGCTGTTACAACTACT AACTATGCCAACTGGGTCCAAGAAAAACCAGATCATTTATTCACTGG TCTAATAGGTGGTACCAACAACCGAGCTCCAGGTGTTCCTGCCAGATT CTCAGGCTCCCTGATTGGAGACAAGGCTGCCCTCACCATCACAGGGG CACAGACTGATGATGAGGCAATATATTTCTGTGCTCTATGGTACAGCA ACCGCTGGGTGTTCGGTGGAGGAACCAAACTGACTGTCCTAGGCCAG CCCAAGTCTTCGCCATCAGTCACCCTGTTTCCACCTTCCTCTGAAGAG CTCGAGACTAACAAGGCCACACTGGTGTGTACGATCACTGATTTCTAC CCAGGTGTGGTGACAGTGGACTGGAAGGTAGATGGTACCCCTGTCAC TCAGGGTATGGAGACAACCCAGCCTTCCAAACAGAGCAACAACAAGT ACATGGCTAGCAGCTACCTGACCCTGACAGCAAGAGCATGGGAAAGG CATAGCAGTTACAGCTGCCAGGTCACTCATGAAGGTCACACTGTGGA GAAGAGTTTGTCCCGTGCTGACTGTTCC* | 34 |
| Light Chain with leader sequence | ATGGCCTGGATTTCACTTATACTCTCTCCTGGCTCTCAGCTCAGGG <u>GCCATTTCC</u>CAGGCTGTTGTGACTCAGGAATCTGCACTCACCACATCA CCTGGTGAAACAGTCACACTCACTTGTCGCTCAAGTACTGGGGCTGTT ACAACTACTAACTATGCCAACTGGGTCCAAGAAAAACCAGATCATTT ATTCACTGGTCTAATAGGTGGTACCAACAACCGAGCTCCAGGTGTTCC TGCCAGATTCTCAGGCTCCCTGATTGGAGACAAGGCTGCCCTCACCAT CACAGGGGCACAGACTGATGATGAGGCAATATATTTCTGTGCTCTAT GGTACAGCAACCGCTGGGTGTTCGGTGGAGGAACCAAACTGACTGTC CTAGGCCAGCCCAAGTCTTCGCCATCAGTCACCCTGTTTCCACCTTCC TCTGAAGAGCTCGAGACTAACAAGGCCACACTGGTGTGTACGATCAC TGATTTCTACCCAGGTGTGGTGACAGTGGACTGGAAGGTAGATGGTA CCCCTGTCACTCAGGGTATGGAGACAACCCAGCCTTCCAAACAGAGC AACAACAAGTACATGGCTAGCAGCTACCTGACCCTGACAGCAAGAGC ATGGGAAAGGCATAGCAGTTACAGCTGCCAGGTCACTCATGAAGGTC ACACTGTGGAGAAGAGTTTGTCCCGTGCTGACTGTTCC* | 35 |
| VL CDR1 | CGCTCAAGTACTGGGGCTGTTACAACTACTAACTATGCCAAC | 36 |
| VL CDR2 | GGTACCAACAACCGAGCTCCA | 37 |
| VL CDR3 | GCTCTATGGTACAGCAACCGCTGGGTG | 38 |
| VL FR1 | CAGGCTGTTGTGACTCAGGAATCTGCACTCACCACATCACCTGGTGAA ACAGTCACACTCACTTGT | 39 |
| VL FR2 | TGGGTCCAAGAAAAACCAGATCATTTATTCACTGGTCTAATAGGT | 40 |
| VL FR3 | GGTGTTCCTGCCAGATTCTCAGGCTCCCTGATTGGAGACAAGGCTGCC CTCACCATCACAGGGGCACAGACTGATGATGAGGCAATATATTTCTG T | 41 |
| VL FR4 | TTCGGTGGAGGAACCAAACTGACTGTCCTA | 42 |
| LC Variable | CAGGCTGTTGTGACTCAGGAATCTGCACTCACCACATCACCTGGTGAA ACAGTCACACTCACTTGTCGCTCAAGTACTGGGGCTGTTACAACTACT AACTATGCCAACTGGGTCCAAGAAAAACCAGATCATTTATTCACTGG TCTAATAGGTGGTACCAACAACCGAGCTCCAGGTGTTCCTGCCAGATT CTCAGGCTCCCTGATTGGAGACAAGGCTGCCCTCACCATCACAGGGG CACAGACTGATGATGAGGCAATATATTTCTGTGCTCTATGGTACAGCA ACCGCTGGGTGTTCGGTGGAGGAACCAAACTGACTGTCCTA | 43 |
| LC Constant | GGCCAGCCCAAGTCTTCGCCATCAGTCACCCTGTTTCCACCTTCCTCT GAAGAGCTCGAGACTAACAAGGCCACACTGGTGTGTACGATCACTGA TTTCTACCCAGGTGTGGTGACAGTGGACTGGAAGGTAGATGGTACCC CTGTCACTCAGGGTATGGAGACAACCCAGCCTTCCAAACAGAGCAAC AACAAGTACATGGCTAGCAGCTACCTGACCCTGACAGCAAGAGCATG GGAAAGGCATAGCAGTTACAGCTGCCAGGTCACTCATGAAGGTCACA CTGTGGAGAAGAGTTTGTCCCGTGCTGACTGTTCC* | 44 |

*This sequence may include a stop sequence, such as TGA
Leader sequence is underlined.

Example 2

This example provides a comparison of the anti-NGly-I antibody of the present disclosure to the previously-described and/or commercially-available anti-NGly-1 antibodies listed in Table 3.

FIGS. 4-9 describe the conditions used and results obtained.

TABLE 3

Antibodies Tested: NGly-1 Specificity

| Source | MW of protein | Dilution | Source | Cat # |
|---|---|---|---|---|
| Mouse monoclonal (anti-mouse peptide) | 66 kDa | 1:2000 (tissues) 1:2000 (cell lines) | JAX Monoclonal Service | |
| Rabbit polyclonal | 66 kDa | 1:400 | Gift from Dr. Tadashi Suzuki | Riken.jp |
| Rabbit polyclonal | 74 kDa | 1:50 (tissues) 1:100 (cell lines) | SIGMA-ALDRICH | HPA036825 |
| Rabbit polyclonal (anti-human amino acids 327-538) | 74 kDa | 1:20 (tissues) 1:100 (cell line) | ABCAM | ab197107 |
| Rabbit polyclonal (anti human amino acids 1-300) | 66 kDa | 1:250 (tissues) 1:250 (cell lines) | EnCor Biotechnology | RPCA-NGLY1 |

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

---

What is claimed is:

1. An antibody that binds specifically to N-glycanase 1 and comprises a heavy chain and a light chain, wherein
the heavy chain comprises
   (a) a CDR1 comprising the sequence of SEQ ID NO: 3,
   (b) a CDR2 comprising the sequence of SEQ ID NO: 4, and
   (c) a CDR3 comprising the sequence of SEQ ID NO: 5, and/or
the light chain comprises
   (a) a CDR1 comprising the sequence of SEQ ID NO: 14,
   (b) a CDR2 comprising the sequence of SEQ ID NO: 15, and
   (c) a CDR3 comprising the sequence of SEQ ID NO: 16.

2. The antibody of claim 1, wherein the heavy chain comprises: a framework region that is at least 90% or at least 95% identical to the sequence of SEQ ID NO: 6; a framework region that is at least 90% or at least 95% identical to the sequence of SEQ ID NO: 7; a framework region that is at least 90% or at least 95% identical to the sequence of SEQ ID NO: 8; and/or a framework region that is at least 90% or at least 95% identical to the sequence of SEQ ID NO:9.

3. The antibody of claim 1, wherein the heavy chain comprises a variable region that is at least 90% or at least 95% identical to the sequence of SEQ ID NO: 10.

4. The antibody of claim 1, wherein the heavy chain comprises a constant region that is at least 90% or at least 95% identical to the sequence of SEQ ID NO: 11.

5. The antibody of claim 1, wherein the heavy chain comprises the sequence of SEQ ID NO: 1.

6. The antibody of claim 1, wherein the light chain comprises: a framework region that is at least 90% identical to the sequence of SEQ ID NO: 17; a framework region that is at least 90% identical to the sequence of SEQ ID NO: 18;

a framework region that is at least 90% identical to the sequence of SEQ ID NO: 19; and/or a framework region that is at least 90% identical to the sequence of SEQ ID NO: 20.

7. The antibody of claim 1, wherein the light chain comprises a variable region that is at least 90% or at least 95% identical to the sequence of SEQ ID NO: 21.

8. The antibody of claim 1, wherein the light chain comprises a constant region that is at least 90% or at least 95% identical to the sequence of SEQ ID NO: 22.

9. The antibody of claim 1, wherein the light chain comprises the sequence of SEQ ID NO: 12.

10. The antibody of claim 1, further comprising a detectable label.

11. A composition comprising the antibody of claim 1.

12. A kit comprising the antibody of claim 1 and a reagent for detecting the antibody.

* * * * *